US 7,727,239 B2

(12) United States Patent
Justin et al.

(10) Patent No.: US 7,727,239 B2
(45) Date of Patent: Jun. 1, 2010

(54) MILLING SYSTEM WITH GUIDE PATHS AND RELATED METHODS FOR RESECTING A JOINT ARTICULATION SURFACE

(75) Inventors: Daniel F. Justin, Logan, UT (US);
Robert A. Hodorek, Warsaw, IN (US);
E. Marlowe Goble, Logan, UT (US);
Carlyle J. Creger, Logan, UT (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

(21) Appl. No.: 11/149,912

(22) Filed: Jun. 10, 2005

(65) Prior Publication Data
US 2006/0293682 A1   Dec. 28, 2006

(51) Int. Cl.
*A61B 17/60* (2006.01)

(52) U.S. Cl. ...................................... 606/88; 606/86 R

(58) Field of Classification Search .................. 606/79, 606/86–89, 96, 86 R
See application file for complete search history.

(56) References Cited

U.S. PATENT DOCUMENTS

| 3,748,662 | A |   | 7/1973  | Helfet |  |
|-----------|---|---|---------|--------|--|
| 4,719,908 | A |   | 1/1988  | Averill et al. |  |
| 4,964,868 | A |   | 10/1990 | Bloebaum |  |
| 5,035,699 | A |   | 7/1991  | Coates |  |
| 5,037,439 | A |   | 8/1991  | Albrektsson et al. |  |
| 5,100,409 | A |   | 3/1992  | Coates et al. |  |
| 5,176,684 | A |   | 1/1993  | Ferrante et al. |  |
| 5,312,408 | A | * | 5/1994  | Brown ........................ 606/80 |  |
| 5,334,205 | A | * | 8/1994  | Cain .......................... 606/96 |  |
| 5,344,423 | A | * | 9/1994  | Dietz et al. ................. 606/87 |  |
| 5,346,496 | A |   | 9/1994  | Penning |  |
| D357,315  | S | * | 4/1995  | Dietz ........................ D24/140 |  |
| 5,413,606 | A |   | 5/1995  | Fisk et al. |  |
| 5,417,695 | A | * | 5/1995  | Axelson, Jr. ................. 606/89 |  |
| 5,474,559 | A |   | 12/1995 | Bertin et al. |  |
| 5,484,446 | A | * | 1/1996  | Burke et al. ................. 606/87 |  |
| 5,486,180 | A |   | 1/1996  | Dietz et al. |  |
| D376,202  | S | * | 12/1996 | Burke et al. ............... D24/140 |  |
| 5,609,642 | A |   | 3/1997  | Johnson et al. |  |

(Continued)

FOREIGN PATENT DOCUMENTS

EP   0 554 959 A1   8/1993

(Continued)

OTHER PUBLICATIONS

Partial Search Report from related EP application 06736184.0 (Published as EP1887951).

*Primary Examiner*—Thomas C Barrett
*Assistant Examiner*—James L. Swiger
(74) *Attorney, Agent, or Firm*—Baker & Daniels LLP

(57) ABSTRACT

A milling system for use in resecting at least a portion of a joint articulation surface of a bone includes an alignment guide having a top surface and an opposing bottom surface with an opening extending therebetween. Fasteners are used to secure the alignment guide to the bone so that the alignment guide is suspended above the bone. A template is removably mounted to the alignment guide so that a plurality of guide paths extending through the template are aligned with the opening in the alignment guide. A mill extends down through the guide path and has a burr on the end thereof for resecting the bone.

23 Claims, 16 Drawing Sheets

U.S. PATENT DOCUMENTS

| | | | |
|---|---|---|---|
| 5,634,927 A | 6/1997 | Houston et al. | |
| 5,653,714 A | 8/1997 | Dietz et al. | |
| 5,709,689 A | 1/1998 | Ferrante et al. | |
| 5,743,915 A | 4/1998 | Bertin et al. | |
| 5,755,803 A | 5/1998 | Haines et al. | |
| 5,769,855 A | 6/1998 | Bertin et al. | |
| 5,860,981 A | 1/1999 | Bertin et al. | |
| 5,885,035 A | 3/1999 | Hoffschneider | |
| 5,908,424 A * | 6/1999 | Bertin et al. | 606/88 |
| 6,063,091 A | 5/2000 | Lombardo et al. | |
| 6,132,468 A | 10/2000 | Mansmann | |
| 6,159,216 A * | 12/2000 | Burkinshaw et al. | 606/88 |
| 6,355,045 B1 * | 3/2002 | Gundlapalli et al. | 606/88 |
| 6,436,101 B1 | 8/2002 | Hamada | |
| 6,482,209 B1 | 11/2002 | Engh et al. | |
| 6,554,838 B2 * | 4/2003 | McGovern et al. | 606/87 |
| 6,620,168 B1 * | 9/2003 | Lombardo et al. | 606/88 |
| 6,712,824 B2 * | 3/2004 | Millard et al. | 606/87 |
| 6,969,393 B2 | 11/2005 | Pinczewski et al. | |
| 2002/0019637 A1 | 2/2002 | Frey et al. | |
| 2002/0198528 A1 | 12/2002 | Engh et al. | |
| 2003/0028196 A1 | 2/2003 | Bonutti | |
| 2003/0130665 A1 | 7/2003 | Pinczewski et al. | |
| 2005/0015153 A1 | 1/2005 | Goble et al. | |
| 2005/0143745 A1 | 6/2005 | Hodorek et al. | |
| 2005/0143831 A1 | 6/2005 | Justin et al. | |
| 2005/0192588 A1 | 9/2005 | Garcia | |
| 2006/0009776 A1 | 1/2006 | Justin | |
| 2006/0009853 A1 | 1/2006 | Justin et al. | |
| 2006/0009854 A1 | 1/2006 | Justin | |
| 2006/0009855 A1 | 1/2006 | Goble et al. | |
| 2006/0167460 A1 | 7/2006 | Pinczewski et al. | |
| 2006/0184176 A1 * | 8/2006 | Straszheim-Morley et al. | 606/88 |
| 2006/0200161 A1 * | 9/2006 | Plaskos et al. | 606/88 |
| 2006/0276796 A1 | 12/2006 | Creger | |
| 2007/0288029 A1 | 12/2007 | Justin | |

FOREIGN PATENT DOCUMENTS

| | | |
|---|---|---|
| EP | 0647432 A1 | 4/1995 |
| EP | 0 502 737 B1 | 9/2002 |
| EP | 1550419 A2 | 7/2005 |
| EP | 1550419 A3 | 7/2005 |
| FR | 2682589 | 4/1993 |
| WO | WO 91/06260 | 5/1991 |
| WO | WO 98/04202 | 2/1998 |
| WO | WO 2004/002332 A1 | 1/2004 |
| WO | WO 2005/069809 A3 | 8/2005 |

* cited by examiner

US 7,727,239 B2

MILLING SYSTEM WITH GUIDE PATHS AND RELATED METHODS FOR RESECTING A JOINT ARTICULATION SURFACE

CROSS-REFERENCE TO RELATED APPLICATIONS

Not applicable.

BACKGROUND OF THE INVENTION

1. The Field of the Invention

The present invention relates to milling systems and related guides and mills for resecting at least a portion of a joint articulation surface of a bone and mounting an implant thereat.

2. The Relevant Technology

The human body has a variety of movable orthopedic joints such as the knee joint, hip joint, shoulder joint, and the like. These joints are formed by the intersection of two bones. The intersecting end of each bone has a smooth articular surface that is comprised of articular cartilage. As a result of injury, wear, arthritis, disease or other causes, it is occasionally necessary to replace all or part of an orthopedic joint with an artificial implant. This procedure is referred to as a joint replacement or arthroplasty. For example, a total knee arthroplasty comprises cutting off or resecting the articular surfaces at both the distal end of the femur and the proximal end of the tibia. Complementary artificial implants are then mounted on the distal end of the femur and the proximal end of the tibia. Where only a portion of a joint is damaged, a partial joint arthroplasty can be performed. In this procedure, one or more artificial implants replace only a portion of a joint.

Although joint replacement is now a common procedure that has met with popular success, conventional implants and related mounting techniques have significant shortcomings. One significant drawback of many joint replacements is the extended and painful patient recovery. For example, a traditional knee replacement requires an open procedure wherein a relatively large incision is made which severs a portion of the muscle bounding the femur. The large incision is made so as to fully expose the respective ends of the femur and tibia.

This exposure is necessary when using conventional techniques to resect the femur and tibia and to mount the implants. For example, resecting the femur and tibia is typically accomplished by a reciprocating saw which requires substantially full exposure of the respective ends of the femur and tibia. Furthermore, some conventional tibial implants are screwed directly into the resected end face of the tibia. Mounting such screws again requires substantially full exposure of the resected end face. In yet other embodiments, the implants are formed with posts projecting therefrom. The posts are received within sockets formed on the resected end face of the tibia and femur. Forming of the sockets and inserting the posts into the sockets requires substantially full exposure of the resected end face of the tibia and femur.

Substantially the same procedures are often used when resurfacing only a portion of a joint articulation surface. That is, the joint is exposed and a reciprocating saw is used to resect half or a portion of the articular cartilage. The implant is then mounted by using screws or posts. Thus, even in procedures where only a portion of the joint articulation surface is being resurfaced, conventional procedures make an invasive retraction of the soft tissue and remove a large portion of the bone.

In general, the more invasive the surgery, the more painful, difficult, and time consuming the patient recovery. Furthermore, extensive resection of bone not only increases bone trauma but can also make subsequent replacement operations more difficult.

Accordingly, what is needed are systems and methods for preparing a joint articulation surface to receive an implant which are easy to use while minimizing the impact on soft tissue and the amount of bone resection. What is also needed are implants which can be used with such systems that can be mounted with minimum trauma.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to milling systems and related guides, templates, and mills for use in resecting an articulation surface of an orthopedic joint so that an implant can be mounted on the resected surface. As used in the specification and appended claims, the term "articulation surface" is broadly intended to include all surfaces of natural articular cartilage forming a portion of an orthopedic joint and all articulation wear surfaces of a bone forming a portion of orthopedic joint that, as a result of wear, trauma, disease or other causes, have all or a portion of the natural articular cartilage removed.

In the below illustrated embodiment of the present invention, milling systems and related guides, templates, and mills are shown which are specifically designed for mounting a condylar implant at the distal end of a femur. It is appreciated, however, that the illustrated embodiments are simply examples of the present invention and that the same technology can also be used for resecting a portion of the articulation surface at a different location on the same articulation surface or on a variety of other joint surfaces to receive a variety of other different types of implants. By way of example and not by limitation, the present invention can be used for resecting all or a portion of a condyle and then mounting a unicondylar or partial condylar implant.

The present invention can also be used for resecting all or a portion of the trochlear groove of a femur and then mounting an implant thereat. In still other embodiments, the present invention can be used for resurfacing any articulation surface of a knee joint, ankle joint, hip joint, shoulder joint, elbow joint, wrist joint, interfrangial joint, or other joints. As such, the milling systems of the present invention can be used for preparing the articulation surface at the proximal or distal end of the femur, tibia, humors, radius, and ulna and on other articulation surfaces of the scapula, pelvis, bones within the foot and hand, and other bone articulation surfaces.

Figure 1:
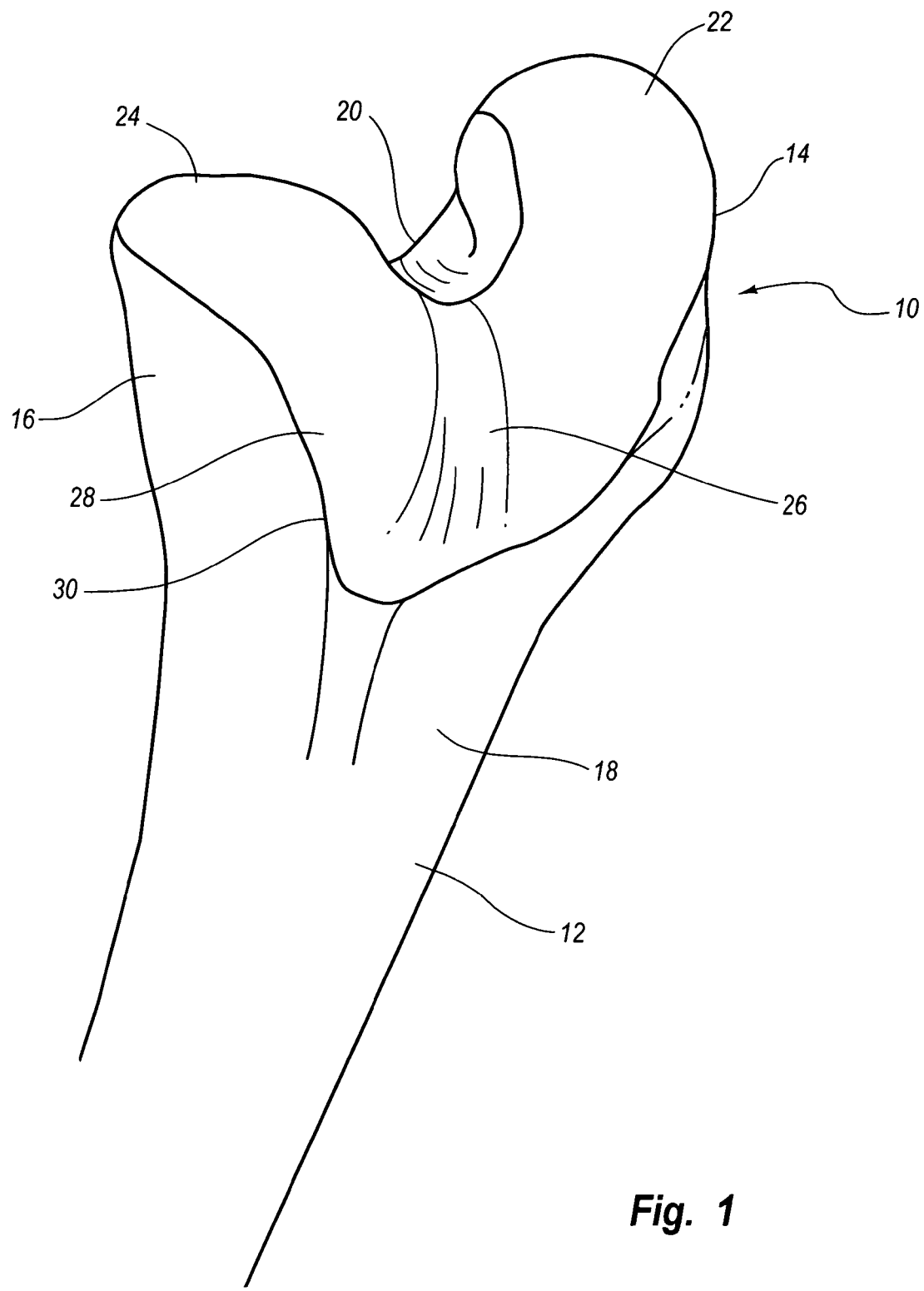
FIG. 1 is a perspective view of the distal end of a femur.

Depicted in FIG. 1 is a distal end 10 of a femur 12. Distal end 10 has a medial side 14 and a lateral side 16 that each extend between an anterior side 18 and a posterior side 20. Distal end 10 of femur 12 terminates at a medial condyle 22 and a lateral condyle 24 with a trochlear groove 26 disposed therebetween. Articular cartilage 28 defines an articulation surface for distal end 10 of femur 12. Articular cartilage 28 terminates at a margin 30.

On occasion, due to arthritis, disease, trauma, or the like, it is necessary to replace all or a portion of medial condyle 22 or lateral condyle 24. In the depicted embodiment of the present invention, the illustrated milling system and related guides, templates, and mills are designed to form a recessed pocket on medial condyle 22 so that an implant can be mounted within the recessed pocket.

Figure 2:
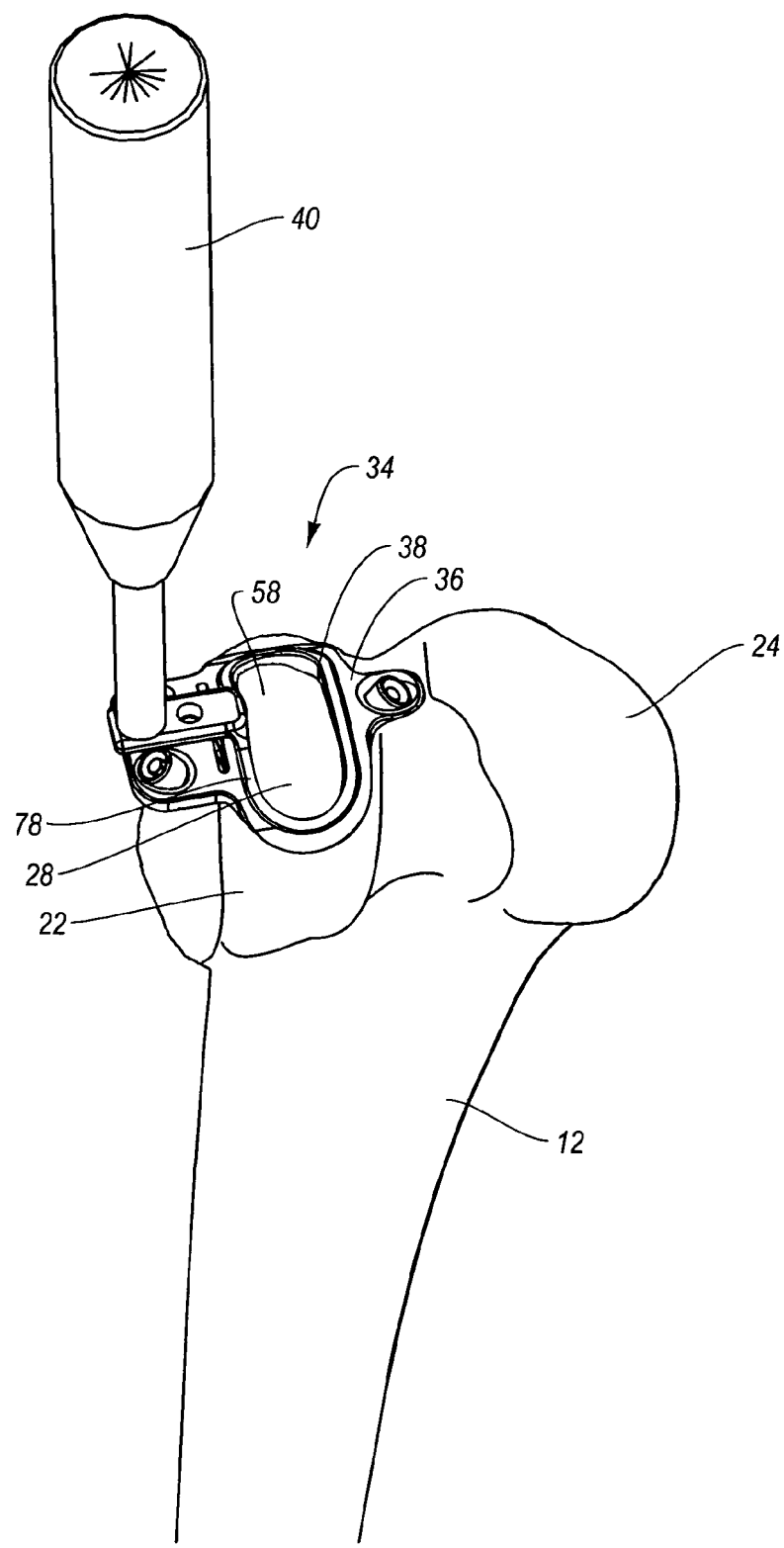
FIG. 2 is a perspective view of the femur shown in FIG. 1 having a guide assembly mounted on a condyle thereof.
Figure 3:
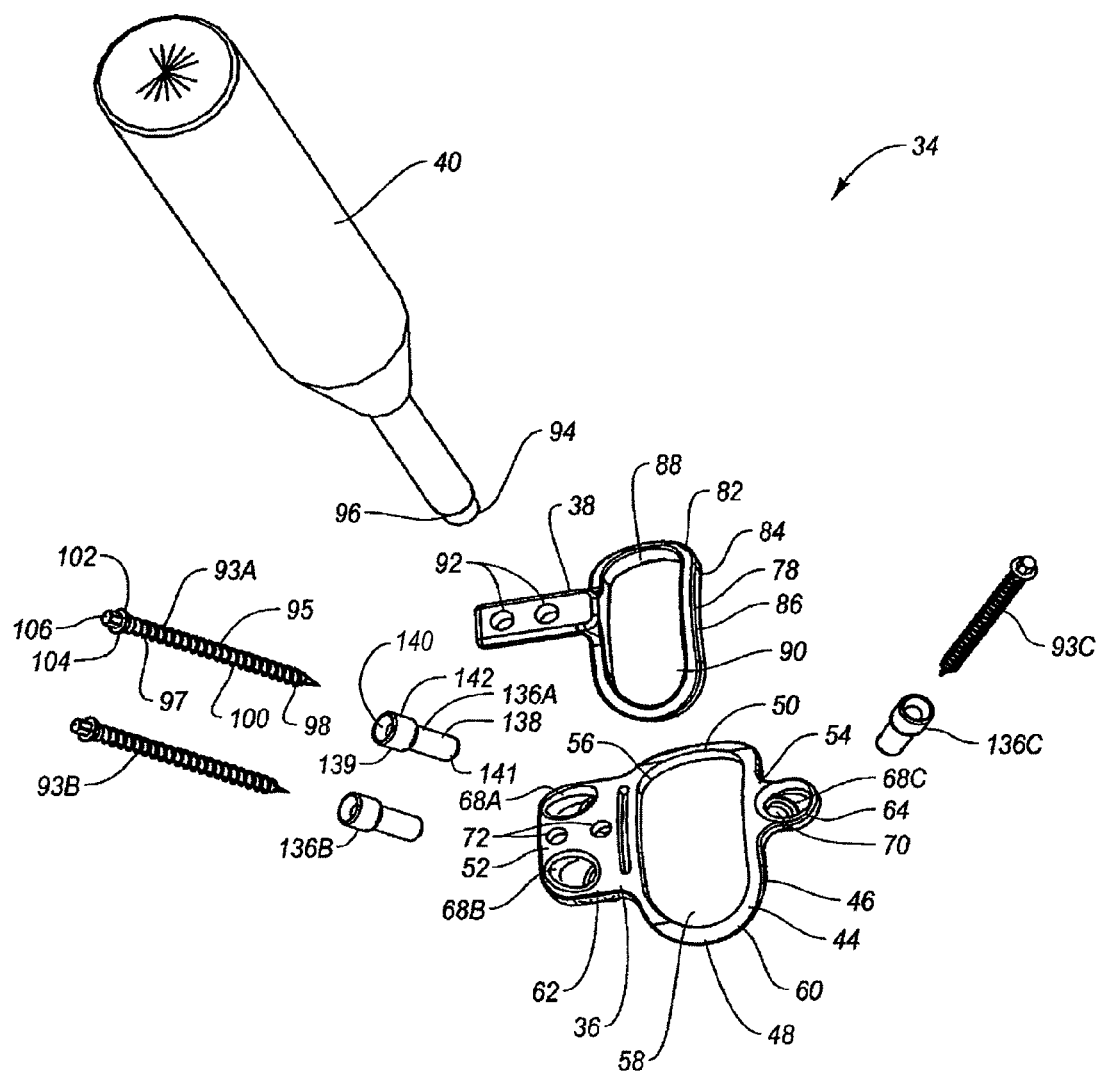
FIG. 3 is an exploded view of the guide assembly shown in FIG. 2.

Depicted in FIG. 2 is a guide assembly 34 incorporating features of the present invention and forming a portion of a milling system. Guide assembly 34 comprises an alignment guide 36, a positioning guide 38, and a handle 40 that removably couples positioning guide 38 on alignment guide 36. As depicted in FIG. 3, alignment guide 36 has a top surface 44 and an opposing bottom surface 46 that each extend between a first end 48 and an opposing second end 50. Surfaces 44 and 46 also extend between a first side 52 and an opposing second side 54.

In the present embodiment alignment guide 36 has a substantially continuous arch extending from first end 48 to opposing second end 50. That is, bottom surface 46 has a substantially constant concave curvature while top surface 44 has a substantially constant convex curvature. This configuration helps to minimize the size of alignment guide 36 to facilitate the greatest ease of insertion during use. In alternative embodiments, however, one or both of top surface 44 and bottom surface 46 can be flat or have any other desired configuration.

To further facilitate complementary positioning of alignment guide 36 over medial condyle 22 while minimizing size, alignment guide 36 can also have an arched curvature extending between opposing sides 52 and 54. That is, bottom surface 46 can have a substantially constant concave curvature extending between opposing sides 52 and 54 while the top surface 44 can have a substantially constant convex curvature. As previously discussed, these surfaces can also be flat or have other configurations. It is appreciated that the configuration of alignment guide 36 can vary depending on the articulation surface being resected. For example, where trochlear groove 26 (FIG. 1) is being resected, alignment guide 36 can have a substantially V-shaped configuration such that alignment guide 36 can sit within trochlear groove 26. Although not required, alignment guide 36 is typically designed so as to have a contour complementary to the contour of the portion of the bone over which alignment guide 36 sits during use.

Alignment guide 36 also has an interior surface 56 that bounds an opening 58 extending through alignment guide 36 between top surface 44 and bottom surface 46. As will be discussed below in greater detail, opening 58 generally corresponds to the size of the pocket that will be formed on the bone. It is appreciated that opening 58 can have a variety of different sizes and shapes depending on the size and location of the area to be resurfaced. In the embodiment depicted, alignment guide 36 completely encircles opening 58 having substantially linear sides and semi-circular ends. In other embodiments, alignment guide 36 can bound only a portion of opening 58. For example, alignment guide can have a substantially C-shaped configuration. In other embodiments, opening 58 can have a substantially circular, elliptical, polygonal, irregular, or other configuration.

Alignment guide 36 can also be defined as having a body portion 60 that bounds opening 58 and has the surfaces as discussed above, a first bracket 62 that projects from side 52 of body portion 60, and a second bracket 64 that projects from side 54 of body portion 60. Both of brackets 62 and 64 project away from body portion 60.

Extending through first bracket 62 are a pair of spaced apart mounting holes 68A and 68B. A mounting hole 68C also extends through second bracket 64. Although not required, in the embodiments depicted each mounting hole 68A-C has an annular shoulder 70 that radially, inwardly projects into the corresponding mounting hole at a location between the opposing ends thereof. As will be discussed below in greater detail, fasteners are designed to pass through mounting holes 68A-C and engage femur 12 so as to secure alignment guide 36 to femur 12. A pair of spaced apart, threaded coupling holes 72 can also be formed on first bracket 62. Coupling holes 72 are used in the attachment of positioning guide 38 to alignment guide 36.

Positioning guide 38 comprises a support 78 having an arm 80 projecting therefrom. Support 78 has a top surface 82 and an opposing bottom surface 84 with an exterior side surface 86 extending therebetween. Exterior side surface 86 has a configuration complementary to interior surface 56 of alignment guide 36 such that support 78 can be received within opening 58 of alignment guide 36. Although not required, support 78 also has an interior surface 88 bounding an opening 90 extending between top surface 82 and opposing bottom surface 84.

Arm 80 projects from top surface 82 and has a pair of spaced apart coupling holes 92 extending therethrough. Coupling holes 92 are configured so that when support 78 of positioning guide 38 is received within opening 58 of alignment guide 36, coupling holes 92 are aligned with coupling holes 72. A threaded tip 94 of handle 40 can then be passed down through one of coupling holes 92 and engaged with a corresponding coupling hole 72. As tip 94 is threaded into coupling hole 72, a shoulder 96 on handle 40 biases against arm 80 so that handle 40 facilitates a releasable, secure engagement between alignment guide 36 and positioning guide 38 as depicted in FIG. 2. Due to the elongated nature of handle 40, handle 40 can be easily held and operated by the surgeon to facilitate proper positioning and removal of guides 36 and 38. It is appreciated that any number of different types of fasteners can be used to removably secure guides 36 and 38 together. For example, clamps, expansion bolts, or other forms of threaded connection can be used. Furthermore, handle 40 is not required and can be replaced with bolts, screws, or other fasteners that extend through one or both sets of coupling holes 72 and 92.

Figure 4:
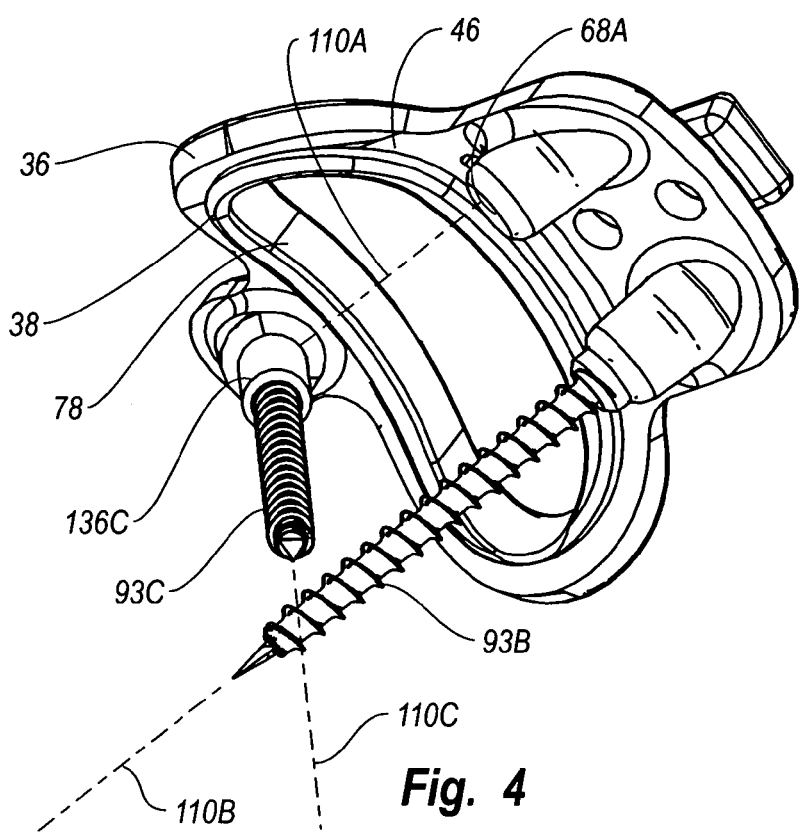
FIG. 4 is a bottom perspective view of the assembled guide assembly shown FIG. 2.

As depicted in FIG. 4, positioning guide 38 is configured such that when positioning guide 38 is mated with alignment guide 36, support 78 of positioning guide 38 projects a distance below bottom surface 46 of alignment guide 36. As a result, positioning guide 38 can be used to mount alignment guide 36 on femur 12 so that alignment guide 36 is suspended above femur 12. Specifically, during use, alignment guide 36 is coupled with positioning guide 38 using handle 40 as discussed above. As depicted in FIG. 2, through the use of handle 40, the coupled guides 36 and 38 are then positioned on medial condyle 22 so that opening 58 of alignment guide 36 is positioned over the portion of articular cartilage 28 that is desired to be resurfaced by an implant.

Here it is again noted that during the positioning, support 78 of positioning guide 38 rests directly against articular cartilage 28 while alignment guide 36 is suspended above or spaced apart from articular cartilage 28 so that it does not directly contact articular cartilage 28. As a result of forming opening 90 on support 78 only a narrow ring portion of support 78 rests on articular cartilage 28. This configuration enables greater stability of positioning guide 38 on articular cartilage 28. In yet other embodiments, support 78 can be formed with a plurality of legs projecting therefrom that rest against the articular cartilage 28. For example, support 78 can be formed with three or more spaced apart legs. The use of three spaced apart legs enables support 78 to be easily stabilized on an uneven surface of articular cartilage 28.

Figure 5:
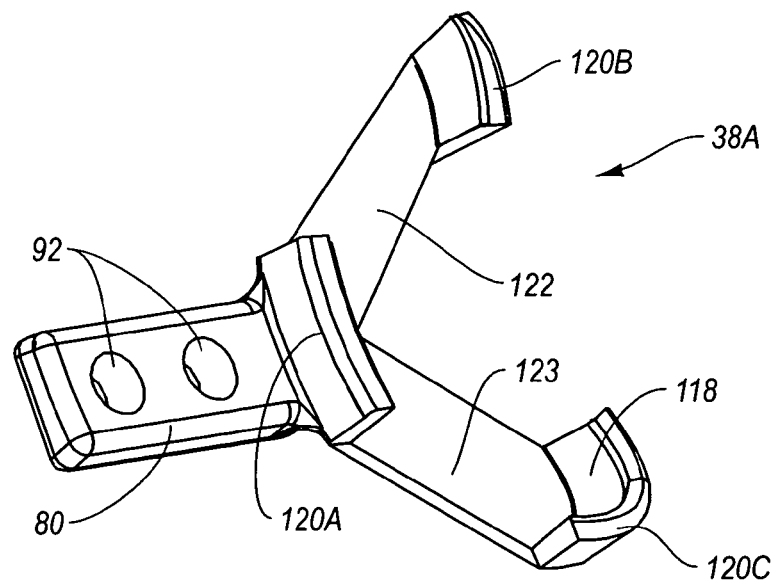
FIG. 5 is a perspective view of an alternative embodiment of the positioning guide shown in FIG. 3.

It is appreciated that support 78 need not have a circular configuration but can have any desired configuration that can be received within opening 58 of alignment guide 36 so as to project below bottom surface 46 and that can be seated in a stable fashion on articular cartilage 28. For example, depicted in FIG. 5 is an alternative embodiment of a positioning guide 38A having a support 118 extending from arm 80. Support 118 comprises three, spaced apart, downwardly projecting legs 120A-C with legs 120B and C being mounted on elongated braces 122 and 123, respectively. During use, legs 120A-C rest directly against articular cartilage 28. The configuration of positioning guide 38 can vary depending on the configuration of the articulation cartilage 28 to be removed.

Once positioning guide 38 is seated on articulation cartilage 28, fasteners are then used to removably secure alignment guide 36 to femur 12. Specifically, as depicted in FIG. 3, in one embodiment of the present invention means are provided for securing alignment guide 36 to femur 12. By way of example and not by limitation, fasteners are designed to pass through mounting holes 68A-C and engage femur 12 so as to removably secure alignment guide 36 to femur 12. In the depicted embodiment, the fasteners comprise threaded screws 93A-C. Each screw 93 comprises an elongated shaft 95 having a first end 97 and an opposing second end 98. Threads 100 are formed along shaft 95 while an enlarged head 102 is formed at first end 97. In the embodiment depicted, enlarged head 102 comprises a flange 104 that encircles and radially outwardly projects from first end 97. An engagement head 106 extends above flange 104 and has a polygonal or non-circular cross section so that a driver can be connected to engagement head 106 for selective rotation of screws 93.

It is appreciated that enlarged head 102 can be formed with a socket, slot(s), or other engaging surfaces to engage with other types of drivers. Each screw 93A-C is configured so that second end 98 can be received within and slid through a corresponding mounting hole 68A-C of alignment guide 36. Enlarged head 102 is larger than mounting holes 68A-C and thus functions as a stop. In alternative embodiments, screws 93A-C can be replaced with other conventional forms of fasteners such as bone anchors, expansion bolts, barbed shafts, and the like.

Figure 6:
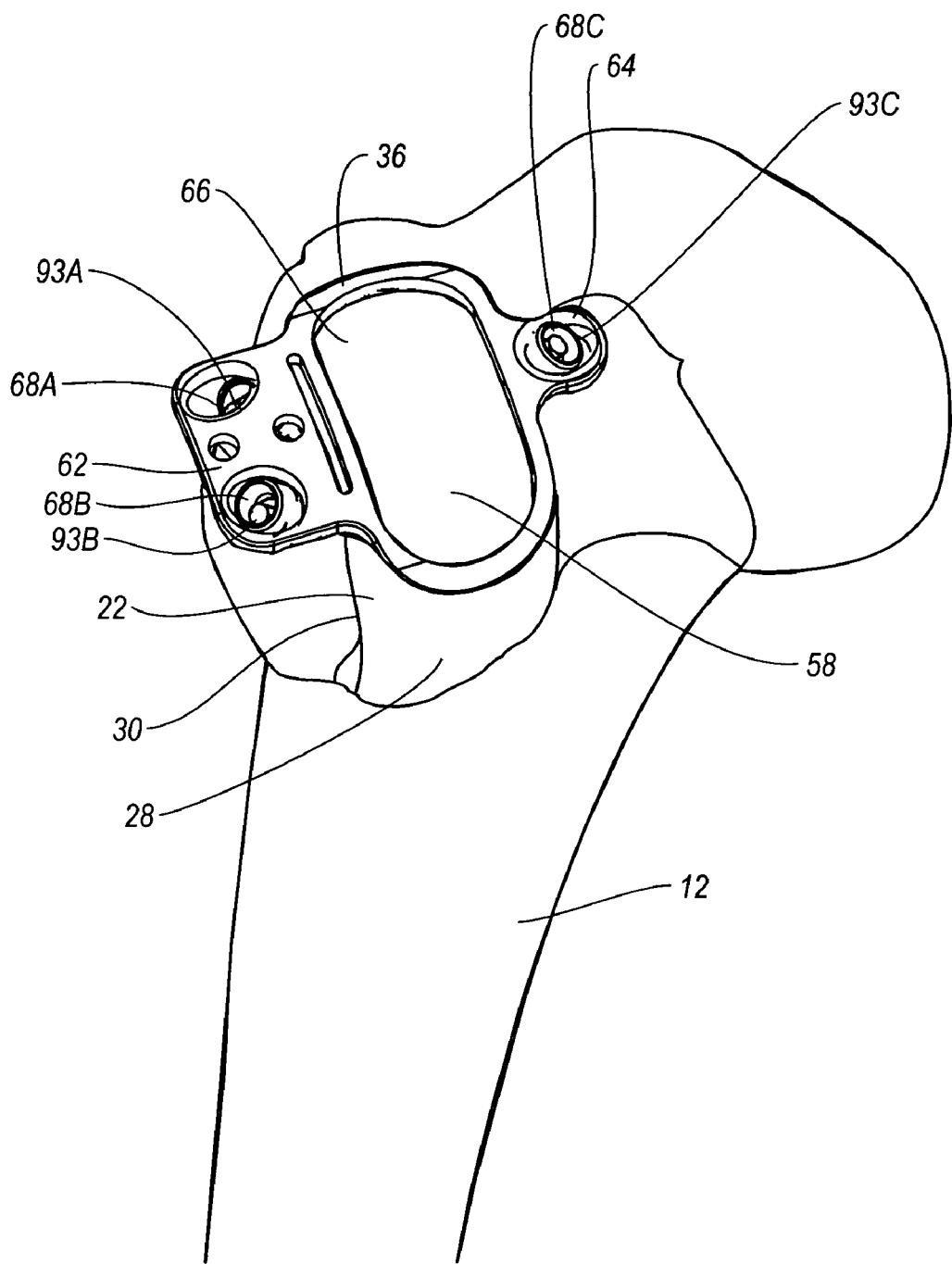
FIG. 6 is a perspective view of the alignment guide shown in FIG. 3 mounted on the femur.

Once guides 36 and 38 are appropriately positioned, screws 93A-C are passed through correspondence mounting holes 68A-C on alignment guide 36 so as to rigidly fix alignment guide 36 at the desired orientation and position. As depicted in FIG. 6, it is appreciated that brackets 62 and 64 and mounting holes 68A-C are positioned so that screws 93A-C screw into femur 12 at margin 30 of articular cartilage 28 or spaced apart from articular cartilage 28. This prevents any unwanted damage to articular cartilage 28.

In one embodiment, screws 93A-C can be used in association with guide sleeves. By way of example, guide sleeves 136A-C are depicted in FIG. 3. Each guide sleeve 136 comprises a tubular stem 138 having a first end 139 and an opposing second end 141. A passageway 140 centrally extends through stem 138 between opposing ends 139 and 141. A flange 142 encircles and radially outwardly projects from first end 139 of stem 138. Each guide sleeve 136A-C is configured so that second end 141 can be received within and slid through a corresponding mounting hole 68A-C. In the depicted embodiment, each mounting hole 68A-C is counter bored so as to form internal constricting shoulder 70 as previously discussed. Flange 142 is sized to rest on shoulder 70 so as to prevent guide sleeves 136A-C from passing completely through corresponding mounting holes 68A-C.

In part, guide sleeves 136A-C function as guides for screws 93A-C. That is, as a result of positioning guide 38 projecting below alignment guide 36, bottom surface 46 of alignment guide 36, and thus the bottom of mounting holes 68A-C, are spaced above femur 12. However, as a result of this gap or space between the bottom of mounting holes 68A-C and femur 12, there is a potential for screws 93A-C to become misaligned from the central longitudinal axis of each corresponding mounting hole 68A-C as screws 93A-C are passed from mounting holes 68A-C to femur 12. This misalignment can cause binding of screws 93A-C against alignment guide 36 which in turn can cause unwanted displacement or improper securing of alignment guide 36. By using guide sleeves 136A-C which extend from mounting holes 68A-C to or adjacent to femur 12, guide sleeves 136A-C help maintain proper orientation and alignment of each screw 93A-C.

Specifically, once guides 36 and 38 are appropriately positioned, each guide sleeve 136A-C is advanced through a corresponding mounting hole 68A-C so that second end 141 of each guide sleeve 136 is disposed adjacent to or butts against articulation surface 28. FIG. 4 shows guide sleeves 136C projecting below bottom surface 46 of alignment guide 36. Screws 93A-C are then passed through guide sleeves 136A-C and screwed into femur 12. Screws 93A-C are advanced until flange 104 biases against the first end of a corresponding guide sleeve 136A-C, thereby securely fixing each guide sleeve 136A-C to femur 12. It is noted that flange 142 of guide sleeves 136A-C need not bias directly against alignment guide 36. Flange 142 primarily functions to prevent guide sleeves 136A-C from falling through mounting holes 68A-C during placement of alignment guide 36. In alternative embodiments, flange 142 can be eliminated.

Here it is noted that each mounting hole 68A-C has a central longitudinal axis 110A-C (FIG. 4), respectively, along which each screw 93A-C is intended to extend. Mounting holes 68A-C are oriented at different angles relative to each other so that merely screwing screws 93A-C into femur 12 through guide sleeves 136A-C positioned within mounting holes 68A-C cause alignment guide 36 to be locked in place. That is, it is not necessary for screws 93A-C to downwardly bias directly against alignment guide 36 to secure alignment guide 36 relative to femur 12. Due to the offset angles of screws 93A-C and thus the offset angles of the guide sleeves 136A-C, it is sufficient if the screws 93A-C merely secure guide sleeves 136 in place to lock alignment guide 36 in place.

Once each screw 93A-C is secured in place so that alignment guide 36 is secured in place, positioning guide 38 is removed from alignment guide 36. This is accomplished by simply unscrewing handle 40 and then lifting off positioning guide 38. As depicted in FIG. 6, alignment guide 36 is then securely fixed to and suspended above femur 12 at the appropriate location. Suspending alignment guide 36 above femur 12 ensures that alignment guide 36 does not unintentionally damage articular cartilage 28 during mounting of alignment guide 36 and/or resecting. Although positioning guide 38 directly sits upon articular cartilage 28, that portion of articular cartilage 28 is ultimately resected and thus any damage caused by positioning guide 38 is irrelevant. In general, the area of articular cartilage 28 bounded by alignment guide 36, i.e., the area within opening 58, is the portion of articular cartilage 28 that will be resected and is referred to herein as cutting surface 66.

Figure 7:
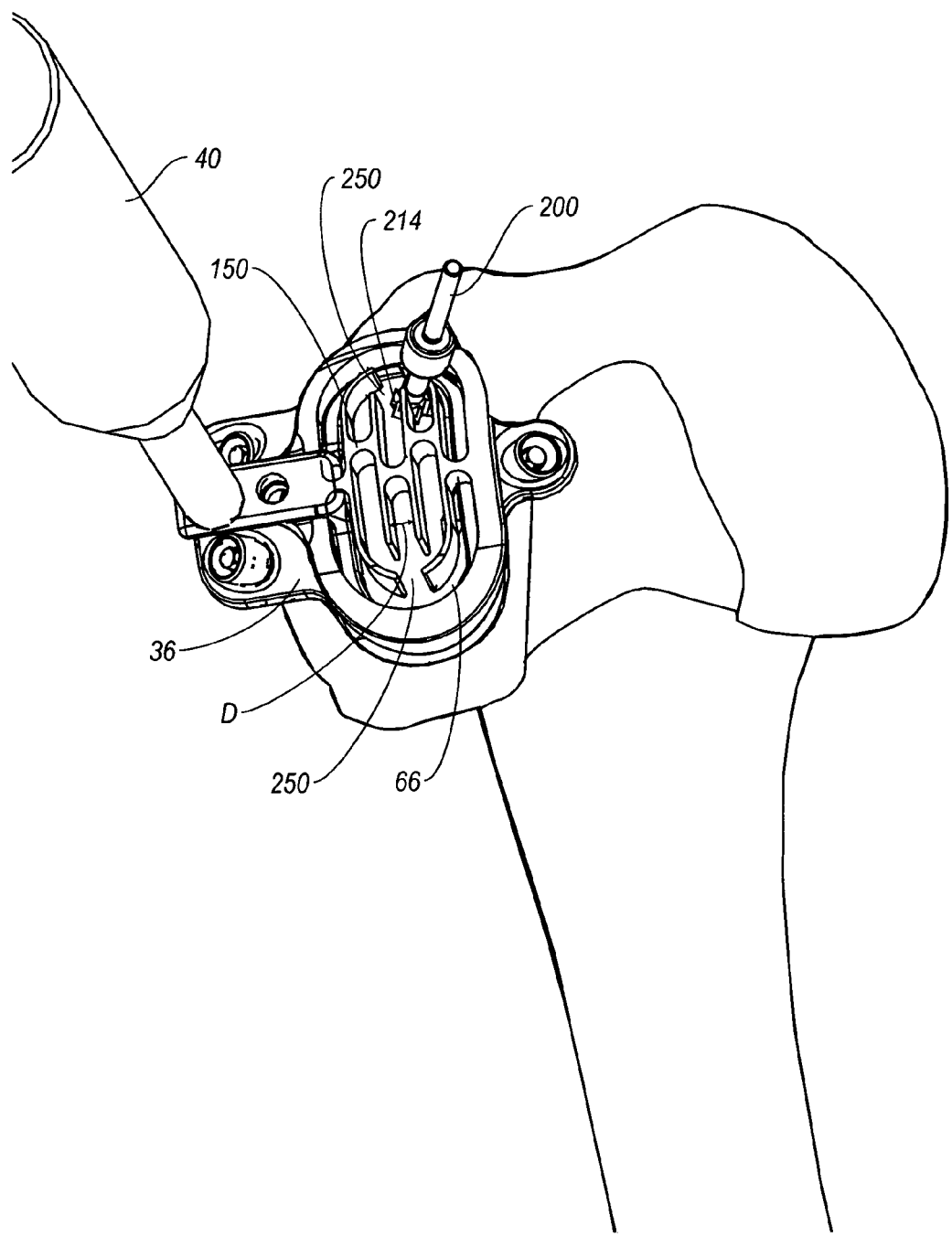
FIG. 7 is a perspective view of the alignment guide shown in FIG. 6 having a template mounted thereon and a mill assembly interacting therewith.
Figure 8A:
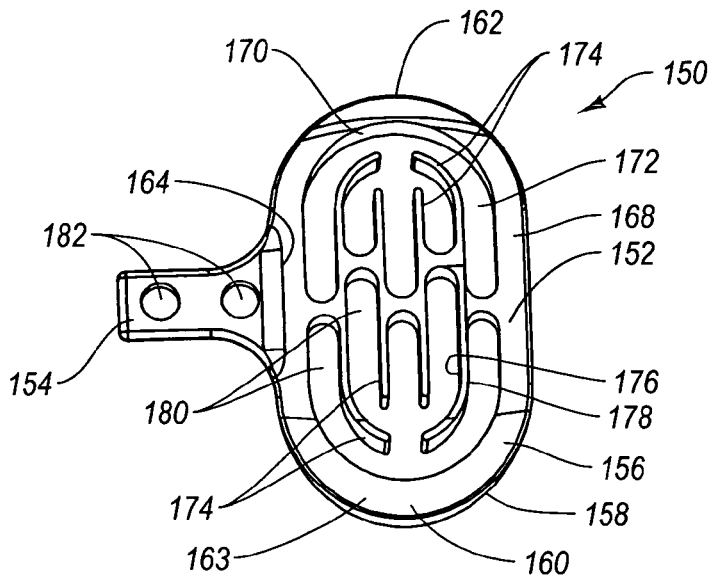
FIG. 8A is a top plan view of the template shown in FIG. 7.

Turning to FIG. 7, once positioning guide 38 is removed from alignment guide 36, a template is mounted on alignment guide 36. Depicted in FIGS. 7 and 8A-8C is one embodiment of a template 150 incorporating features of the present invention which can be used with the inventive milling systems. With reference to FIG. 8A, template 150 comprises a base 152 having an arm 154 projecting therefrom. Base 152 has a top surface 156 and an opposing bottom surface 158 each extending between a first end 160 and an opposing second end 162. Base also has a first side 164 and an opposing second side 168.

Base 152 can be further defined as having an outer body 163 having an interior surface 170 that bounds an opening 172 extending through body 163 from top surface 156 to bottom surface 158. In the embodiment depicted, body 163 has substantially the same configuration as body portion 60 of alignment guide 36 and is designed to rest on top surface 44 thereof. For example, body 163 can have parallel sides that terminate at semi-circular ends. Other shapes such as elliptical, circular, polygonal, irregular, or the like, can also be used. Opening 172 of body 163 can have substantially the same size and configuration as opening 58 of alignment guide 36.

Projecting from interior surface 170 of body 163 into opening 172 are a plurality of interconnected partition walls 174. In general, each partition wall 174 has opposing side faces 176 and 178. Partition walls 174 divide opening 172 into a plurality of guide paths 180, some of which are interconnected. Specifically, guide paths 180 are bounded between opposing side faces of adjacent partition walls 174 and are formed between interior surface 170 of body 163 and a side face on an adjacent partition wall 174. As will be discussed below in greater detail, guide paths 180 function as guides for a mill used in resecting cutting surface 66.

In the depicted embodiment, interior surface 170 and the side surfaces of partition walls 174 are disposed in parallel alignment. That is, in contrast to having surfaces that slope relative to each other so that projections of such surfaces diverge and intersect, projections of the interior and side surfaces of base 152 can all intersect a common plane at right angles. As will be discussed below in greater detail, other designs can also be used.

Figure 8B:
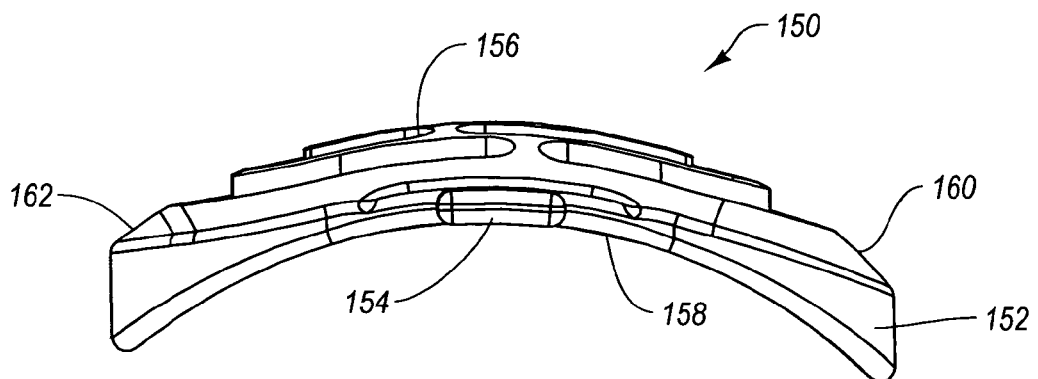
FIG. 8B is an elevated side view of the template shown in FIG. 8A.
Figure 8C:
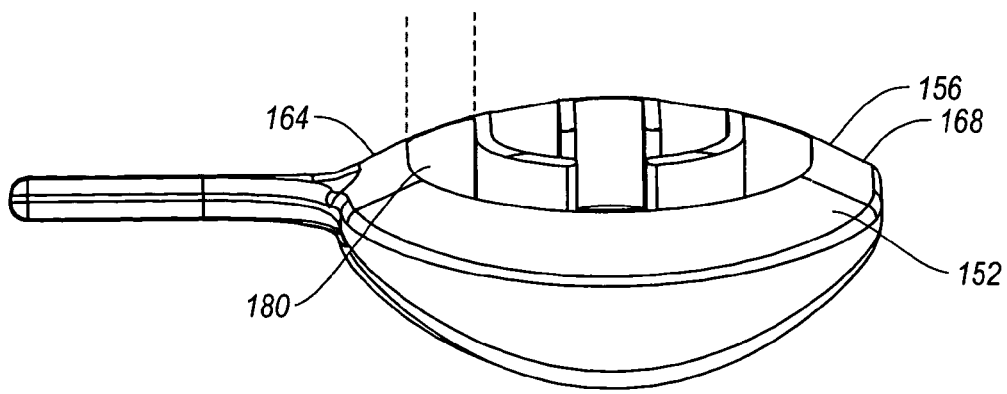
FIG. 8C is an elevated end view of the template shown in FIG. 8A.

Turning to FIG. 8B, base 152 has a substantially constant curvature extending between first end 160 and opposing second end 162. Specifically, top surface 156 has a convex curvature while bottom surface 158 has a concave curvature extending between opposing ends. Similarly, as depicted in FIG. 8C, top surface 156 has a substantially convex curvature extending between opposing sides 164 and 168 while bottom surface 158 can have a complementary concave curvature. In this regard, top surface 156 and bottom surface 158 have a substantially dome-shaped configuration. As will be discussed below in greater detail, the configuration of top surface 156 in part dictates the configuration of the floor of the recessed pocket. Bottom surface 158 of base 152 is typically configured complimentary to top surface 44 of alignment guide 36 but can be other desired shapes.

Returning to FIG. 8A, a pair of spaced apart coupling holes 182 extend through arm 154. Arm 154 and coupling holes 182 are configured such that when base 152 is mounted on alignment guide 36, coupling holes 182 of template 150 are aligned with coupling holes 72 of alignment guide 36. As a result, handle 40 can be used to secure template 150 to alignment guide 36 through alignment holes 72 and 182 in substantially the same manner that position guide 38 was removable attached alignment guide 36, as previously discussed. Again, other removable mounting techniques can be used. It is appreciated that alignment holes 72 and 182 can each comprise one hole or three or more holes. The formation of more than one alignment hole can be used for additional fasteners or for selective placement of handle 40.

Figure 9:
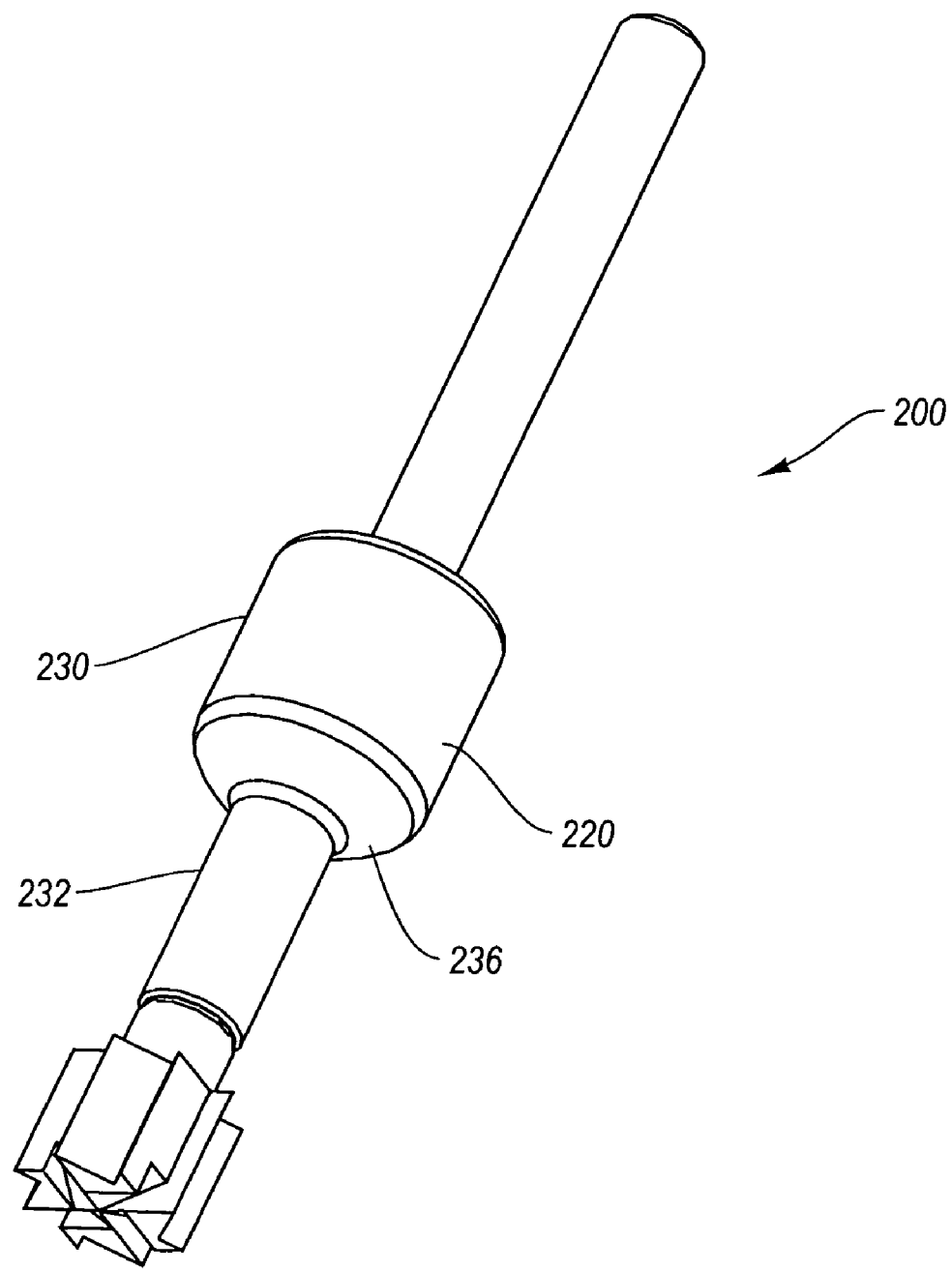
FIG. 9 is a perspective view of the mill assembly shown in FIG. 7.
Figure 10:
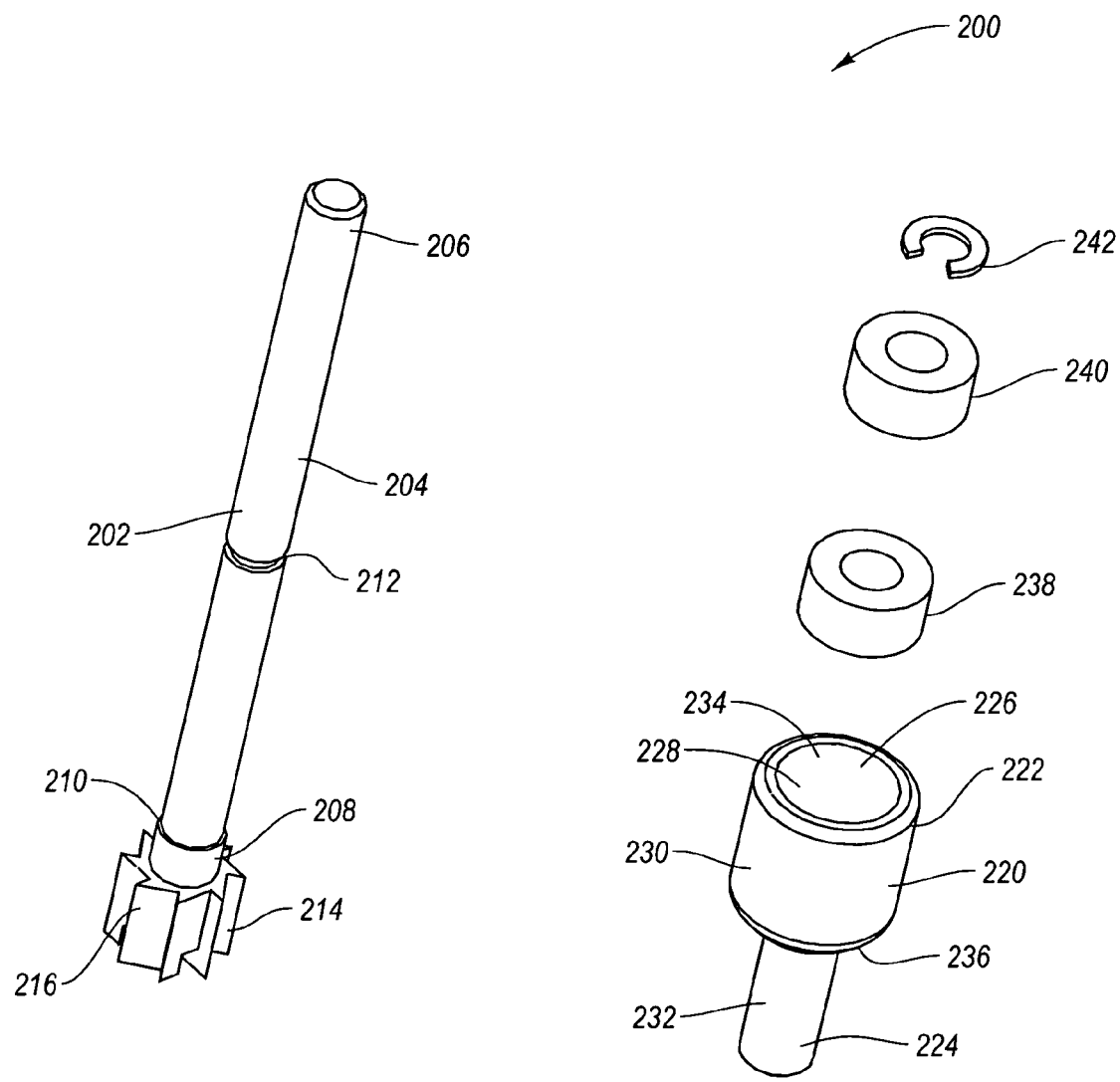
FIG. 10 is an exploded view of the mill assembly shown in FIG. 9.

As shown in FIG. 7, once template 150 is secured to alignment guide 36, a mill assembly 200 is used in conjunction with template 150 to resect cutting surface 66. Depicted in FIGS. 9 and 10 is one embodiment of mill assembly 200 incorporating features of the present invention. Mill assembly 200 comprises a mill 202 having an elongated shaft 204 extending between a first end 206 and an opposing second end 208. Shaft 204 has an annular shoulder 210 encircling and radially outwardly projecting at second end 208. An annular locking groove 212 is centrally formed on shaft 204. Mill 202 further comprises a burr 214 mounted on second end 208 of shaft 204 so that burr 214 radially outwardly projects from shaft 202. Burr 214 is comprised of a plurality of cutting teeth 216 that enables burr 214 to cut from the side and the bottom. As used in the specification and appended claims, the term "burr" is broadly intended to include any arrangement of cutting teeth or cutting surfaces that when mounted on shaft 204 can be used to cut bone when shaft 204 is rotated. For example, in contrast to having one or more defined cutting teeth, burr 214 can also comprise a rough surface that can grind or cut away bone.

Mill assembly 200 further comprises a bearing housing 220. Bearing housing 220 has an interior surface 226 that bounds a passageway 228 extending between a first end 222 and a second end 224. Bearing housing 220 can be further defined as comprising a tubular first sleeve 230 formed at first end 222 that bounds a compartment 234 and a tubular second sleeve 232 formed at second end 224. First sleeve 230 has an outer diameter larger than second sleeve 232 with a rounded tapered shoulder 236 extending between sleeves 230 and 232.

During assembly, second end 224 of bearing housing 220 is advanced over first end 206 of shaft 204 until second end 232 of bearing housing 220 comes to rest on support shoulder 210 of mill 202. A pair of bearings 238 and 240 is also advanced over shaft 204 so as to be received within compartment 234 of first sleeve 230. A clip 242 is then received within locking groove 212 so as to secure bearing housing 220 and bearings 238 and 240 on mill 202. Bearings 238 and 240 can be ball bearings, roller bearings, or other forms of bearings. In one alternative, one or three or more bearings can be used.

Depicted in FIG. 7, during use, burr 214 is passed through template 150 so that shaft 204 is disposed within a guide path 180. In one embodiment, guide paths 180 have a minimum diameter D extending between adjacent partition walls 174 or between the partition walls 174 and interior surface 170 of base 152 that is smaller than the maximum diameter of burr 214. As such, burr 214 is prevented from traveling through or out of guide paths 180. However, guide paths 180 are formed so that an area of intersecting guide paths 180 forms an access area 250 having an area sized so that burr can pass therethrough. Either before or after passing mill 202 through template 150, a drill or other form of driver is coupled with first end 206 of shaft 206 so as to enable rapid rotation shaft 204 about the longitudinal axis thereof.

Figure 11:
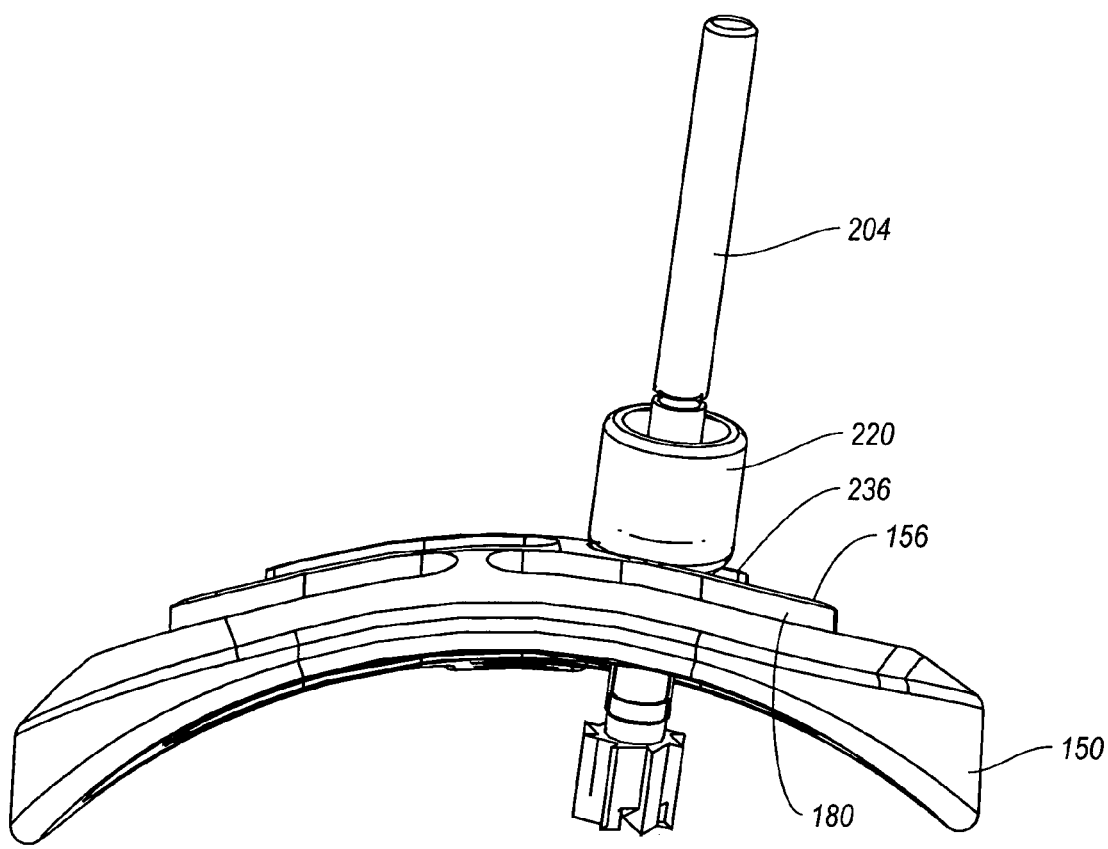
FIG. 11 is an elevated side view of the template shown in FIG. 7 having the mill assembly extending therethrough.

As shaft 204 is rotated, burr 214 cuts away at articular cartridge 28 of cutting surface 66. Burr 214 cuts down through articular cartridge 28 until shoulder 236 of bearing housing 220 comes to rest on top surface 156 of template 150 as shown in FIG. 11. Shoulder 236 thus defines the depth at which burr 214 cuts. During the procedure, the surgeon slowly advances mill assembly 200 along each of guide paths 180 so as to resect cutting surface 66 and thereby form the recessed pocket. Because the cutting depth of burr 214 is regulated by the interaction between shoulder 236 and top surface 156 of template 150, movement of milling assembly 200 about the curved top surface 156 of template 150 produces a recessed pocket having a floor with a contour similar to the contour of top surface 156.

Furthermore, burr 214 has an effective radius that extends from shaft 204 to the maximum outer radius of burr 214. The effective radius is equal to or greater than at least half the thickness of each partition wall 174. As a result, as mill 202 is advanced down a guide path 180 on adjacent sides of a partition wall 174, burr 214 undercuts the partition wall 174 so as to remove all of the articular cartridge directly below the partition wall 174. Burr 176 also undercuts interior surface 170 of template 150.

During the milling process, as shoulder 236 of bearing housing 220 rides along template 150, first sleeve 232 of bearing housing 220 is disposed within the corresponding guide path 180. In one embodiment, each guide path has a diameter substantially equal to but slightly larger then the outer diameter of first sleeve 232 of bearing housing 220. This configuration enables free movement of bearing housing 220 along guide paths 180 but prevents unwanted lateral tipping of mill 202. As a result, the recessed pocket can be formed with greater precision and tolerance. In one embodiment, the minimum diameter of a guide path is typically less than 15% greater than the maximum diameter first sleeve 232 and is typically less than 10% or 5% greater than the maximum diameter first sleeve 232. In alternative embodiments, the minimum diameter of a guide path 180 can be greater than the maximum diameter of burr 214.

Figure 12:
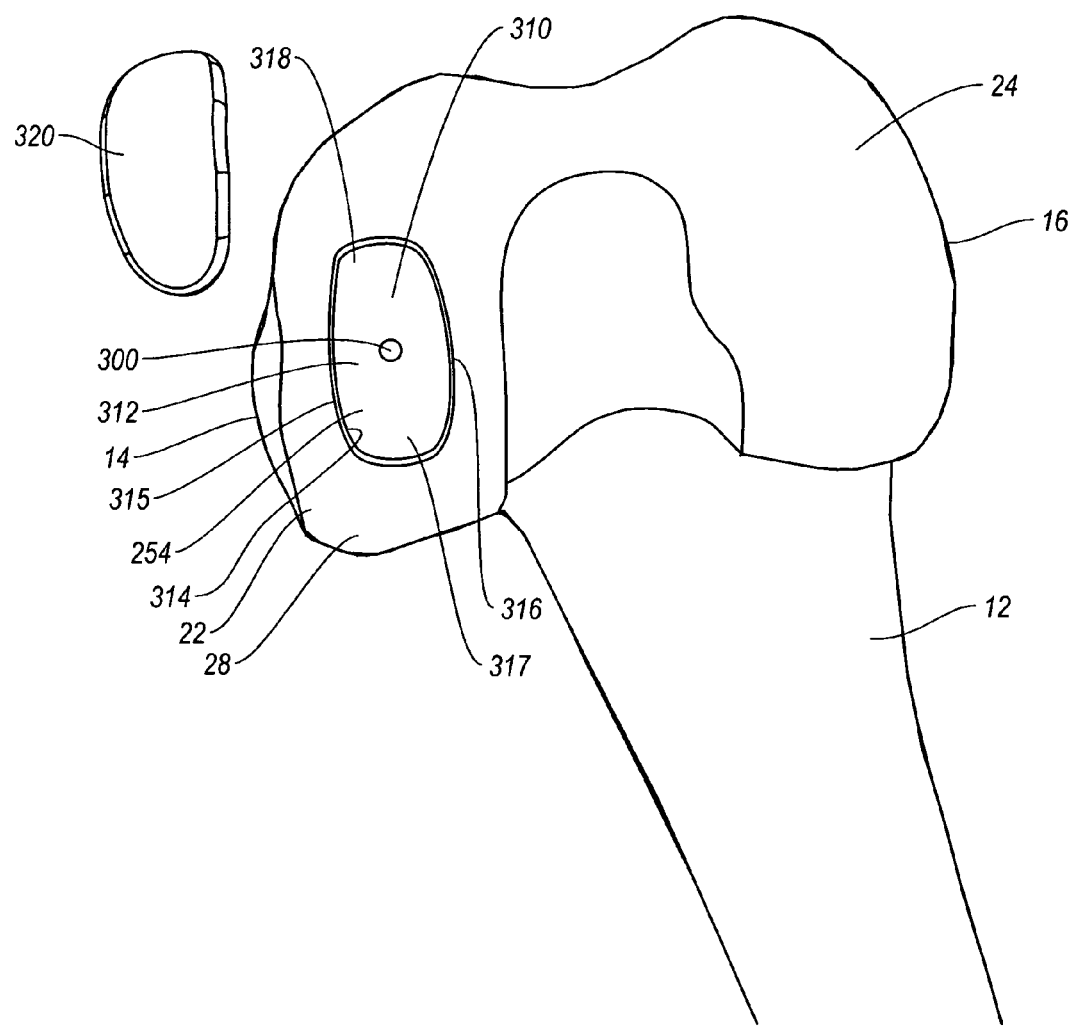
FIG. 12 is a perspective view of the femur shown in FIG. 7 having a recessed pocket formed thereon.

Once mill 202 has been advanced down each of guide paths 180 so as to complete the resection of cutting surface 66, mill assembly 200 is removed. Template 150 and alignment guide 36 can then also be removed, thereby exposing resected pocket 310 as depicted on FIG. 12. Pocket 310 is bounded by a floor 312 having an encircling side wall 314 upstanding around the perimeter thereof. Pocket 310 has opposing sides 315 and 316 that extend between a proximal end 317 and an opposing distal end 318. Due to the controlled movement of mill 202, floor 312 has a convex curvature that extends between proximal end 317 and distal end 318 and a convex curvature that extends between opposing sides 315 and 316. As will be discussed below in greater detail, the configuration of recessed pocket 310 enables the use of a low profile implant having substantially uniform thickness. Furthermore, the formation of pocket 310 produces a stable platform for the implant having a complementary configuration.

Figure 13A:
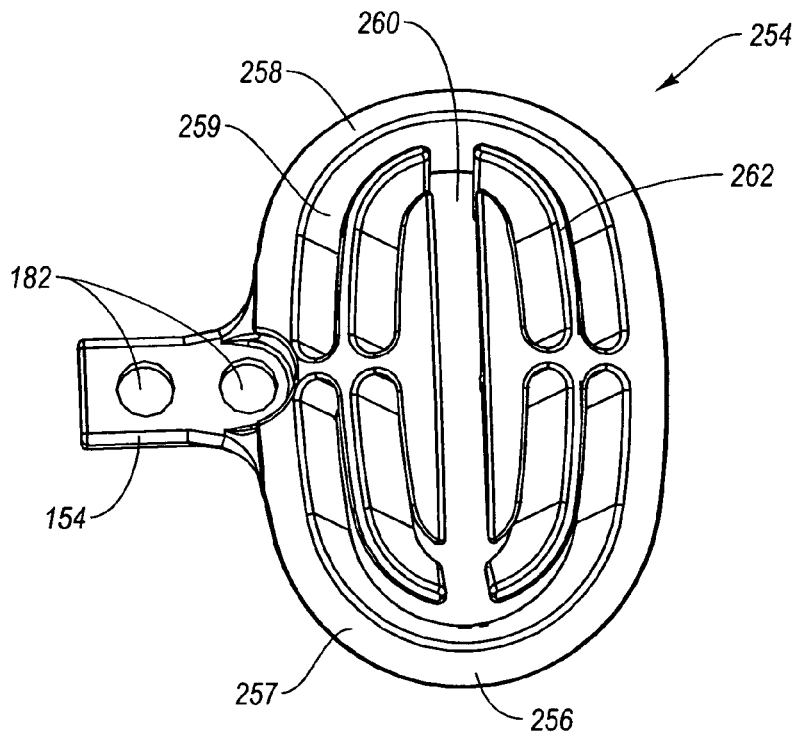
FIG. 13A is a top plan view of an alternative embodiment of the template shown in FIG. 7A.

It is appreciated that template 150 used in forming pocket 310 can come in a variety of different sizes, shapes, and configurations depending on the location, size, and contour of articular cartilage to be removed. Depicted in FIG. 13A is one alternative embodiment of a template 254 that can replace template 150. Template 254 comprises a base 256 having arm 154 projecting therefrom. Base 256 has a top surface 257 having an arched contour substantially the same as top surface 156 of template 150. Base 256 includes an outer body 258 having an interior surface 259 that bounds an opening 260. Projecting from interior surface 259 are a plurality of partition walls 262 that bound a plurality of guide paths 264. By comparing templates 150 and 254, it is appreciated that the partition walls and guide paths, can have any desired configuration, contour and/or layout as long as they enable mill 202 to properly remove articular cartilage 28. In this regard, the partition walls and guide paths can be interconnected, separated, or combinations thereof. The partition walls and guide paths can also be linear, curved, or have other desired orientations.

Figure 13B:
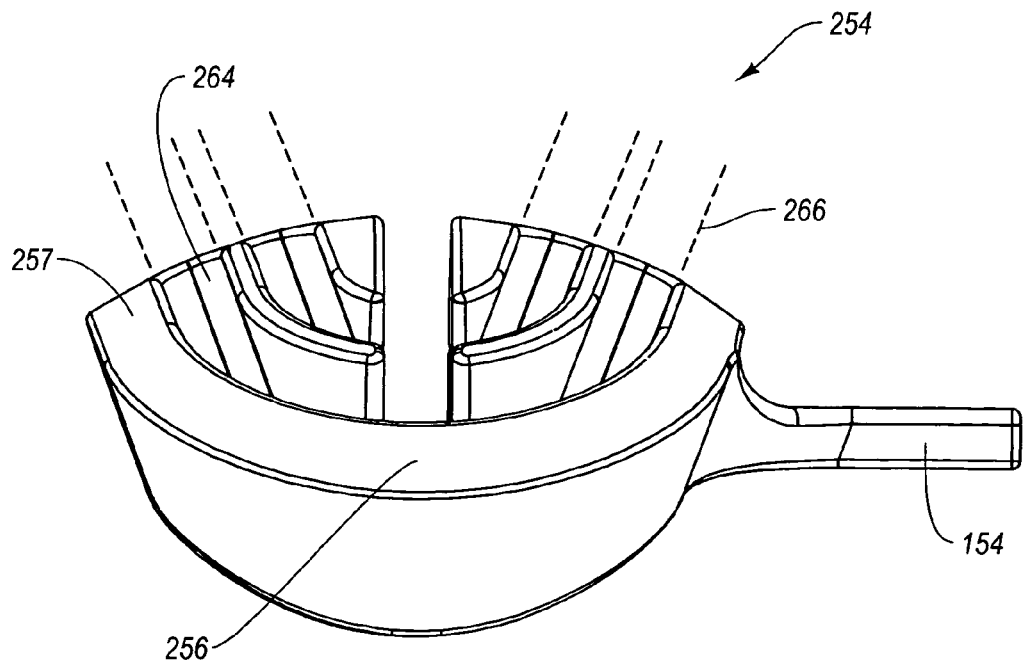
FIG. 13B is an elevated end view of the template shown in FIG. 13A.

Furthermore, in contrast to template 150 wherein the side faces are in parallel alignment as discussed above, in template 254 select side faces of the partition walls 262 are sloped at different angles relative to each other. Specifically, as depicted in FIG. 13B, the various side faces of partition walls 262 and interior surface 259 of body 258 intersect at substantially right angles with top surface 257 of base 256. Expressed in other terms, guide paths 264 projecting from top surface 257 of base 256, as depicted by dashed lines 266, project normal to top surface 257. This is in contrast to template 150, as depicted in FIG. 8C, where many of the guide paths 180 project from top surface 156 at orientations that are not normal to top surface 156. One of the benefits of template 254 is that during use, mill 202 is oriented normal to the final floor 312 of recessed pocket 310. As a result, the use of template 254 results in floor 312 of recessed pocket 310 having a more uniformly smooth, arched surface in comparison to floor 312 resulting from the use of template 150.

Returning to FIG. 12, once recessed pocket 310 is finished, a tunnel 300 can be formed extending from pocket 310 to a location spaced apart from the articular cartilage 28, such as medial side 14 or lateral side 16 of femur 12. Tunnel 300 can be formed by simply using a drill to manually form the tunnel. That is, tunnel 300 can be drilled by starting at recessed pocket 310 and extending to the lateral or medial side of the femur 12. Other techniques, guides and instruments for forming tunnel 300 are disclosed in U.S. patent application Ser. No. 10/901,941, filed Jul. 28, 2004 which is incorporated herein by specific reference.

Figure 14:
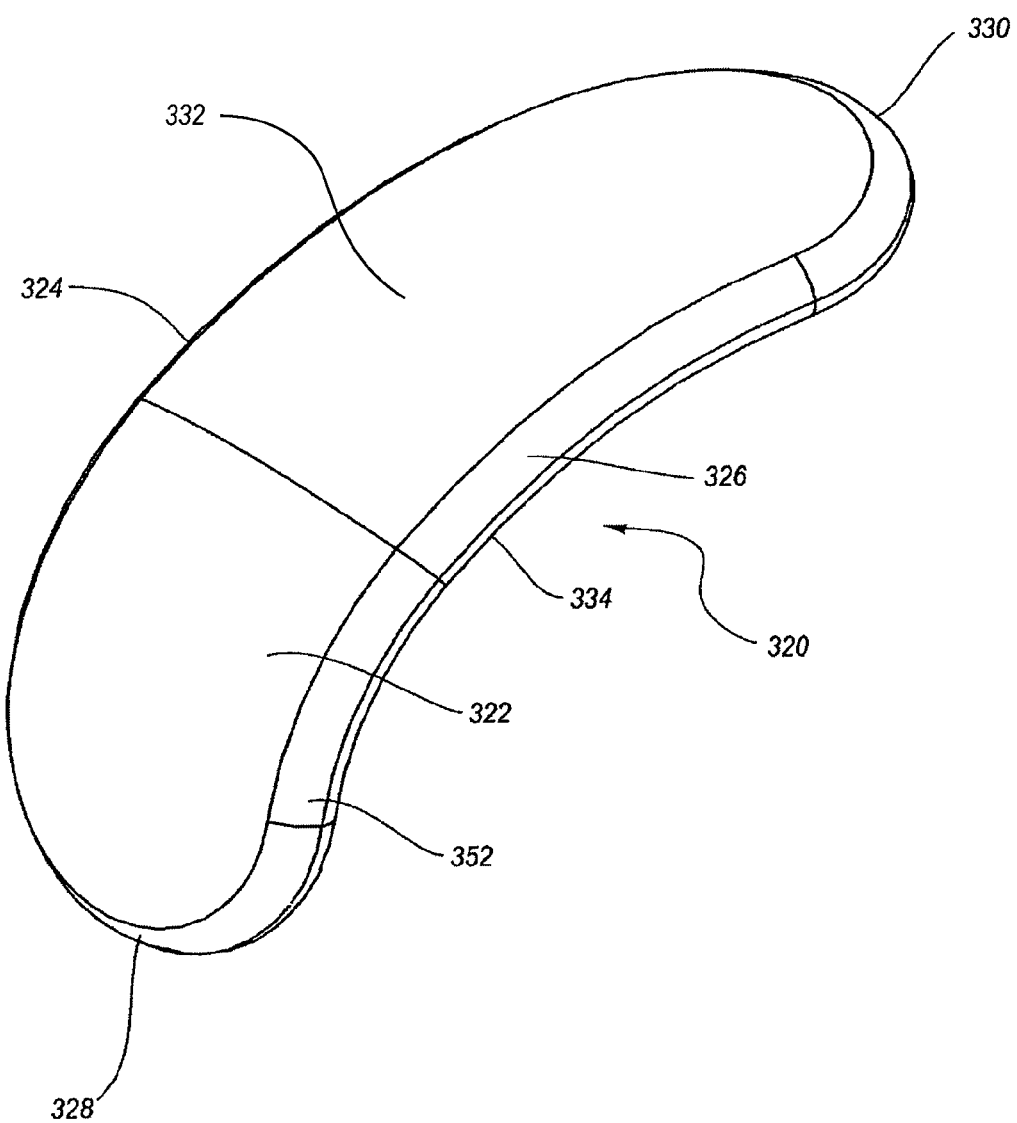
FIG. 14 is a top perspective view of a condylar implant.
Figure 15:
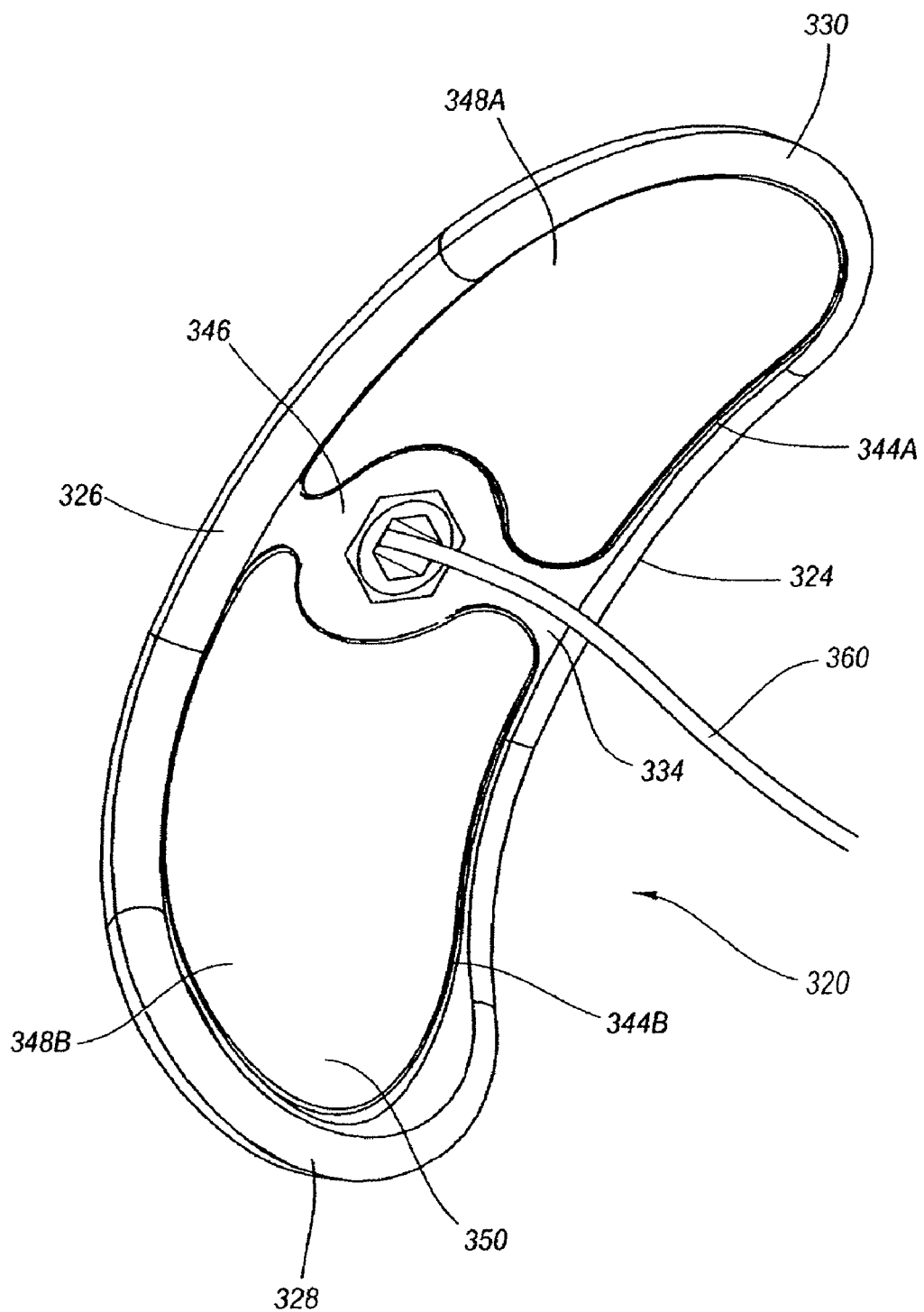
FIG. 15 is a bottom perspective view of the condylar implant shown in FIG. 14.

Once tunnel 300 is formed, an implant is then secured within the recessed pocket 310. Depicted in FIGS. 14 and 15 is one embodiment of a condylar implant 320 incorporating features of the present invention. Condylar implant 320 comprises an elongated body 322 having a first side 324 and an opposing second side 326 that each extend between opposing ends 328 and 330. Body 322 also has a curved articular surface 332 and an opposing bottom surface 334. In one embodiment, articular surface 332 can have a continuous convex curvature that extends between opposing sides 324 and 326 and a continuous convex curvature that extends between opposing ends 328 and 330.

A pair of pockets 344A and B are formed on bottom surface 334 and are separated by a bridge 346. Disposed within each pocket 344A and B is an inlay 348A and B of porous bone ingrowth material. Bridge 346 and inlays 348A and B substantially comprise a bone apposition surface 350. Bone apposition surface 350 can have a configuration complementary to the formation of recessed pocket 310. Bone apposition surface 350 can also have a configuration complementary to articular surface 332. In one embodiment, bone apposition surface 350 can have a continuous concave curvature which extends between opposing sides 324 and 326 and a continuous concave curvature which extends between opposing ends 328 and 330. As a result, condylar implant can have a substantially uniform thickness along its length. In other embodiments, implant 340 may be slightly tapered along a perimeter edge 352 thereof. Thus, at all locations at least 2 mm in from the perimeter edge 352, body 322 can have a thickness extending between the bone apposition surface 350 and the articular surface 322 that does not vary by more than 30%, 20%, or more commonly 15%. Other percentages can also be used. The actual thickness depends on the desired implant and is typically in a range between about 3 mm to about 10 mm.

Connected to bridge 346 is a flexible line 360. As used in the specification and append claims, the term "line" is broadly intended to include wire, cable, cord, suture, braded line, combinations thereof or any other type of flexible filament. The line can be made of metal, alloys, synthetics, composites, or any other desired material. In one embodiment of the present invention the line comprises braded filaments of a cobalt chrome alloy having a diameter in a range between about 0.25 mm to about 5 mm with about 0.5 mm to about 3 mm being more common and about 0.5 mm to about 2 mm being most common. Other dimensions can also be used. The line can be of any desired length.

In one embodiment, the line can also be defined in that for an unsupported length of line of 4 cm, the line has substantially no compressive strength. In yet other embodiments, for an unsupported length of line of 4 cm, the line fails under buckling when an axial compressive load of 0.25 Newtons (N), 1 N, 2 N, 5 N, 20 N, or 50 N is applied. That is, different lines can be used that fail under different loads. Stiffer lines can also be used.

It is also appreciated that the line can be static or resiliently stretchable. In one embodiment where the line is resiliently stretchable, the line can be comprised of a material having shape memory of pseudo elastic properties. One example of such a material is a nickel titanium alloy sold under the name Nitinol. In yet other embodiment, it is appreciated that sections of the line could be replaced with a spring member such as a coiled spring or rubber or bungee type member. It is appreciated that line 360 can be permanently or removably attached to implant 320. Examples of methods for attaching line 360 to implant 320 are disclosed in U.S. patent application Ser. No. 10/901,941 which was previously incorporated by reference.

It is appreciated that implant 320 as discussed above and depicted herein is only one example of an implant that can be used in association with the present invention. In alternative embodiments, implant 320 can have a variety of different sizes, shapes, configurations, components, and other modifications. For example, spikes or other forms of projections can be formed projecting from bone apposition surface 350. Furthermore, conventional implants using conventional mounting techniques can be secured within recessed pocket 310. Examples of alternative implants that can be used with the present invention are disclosed in U.S. patent application Ser. No. 10/901,941 which was previously incorporated by reference.

Figure 16:
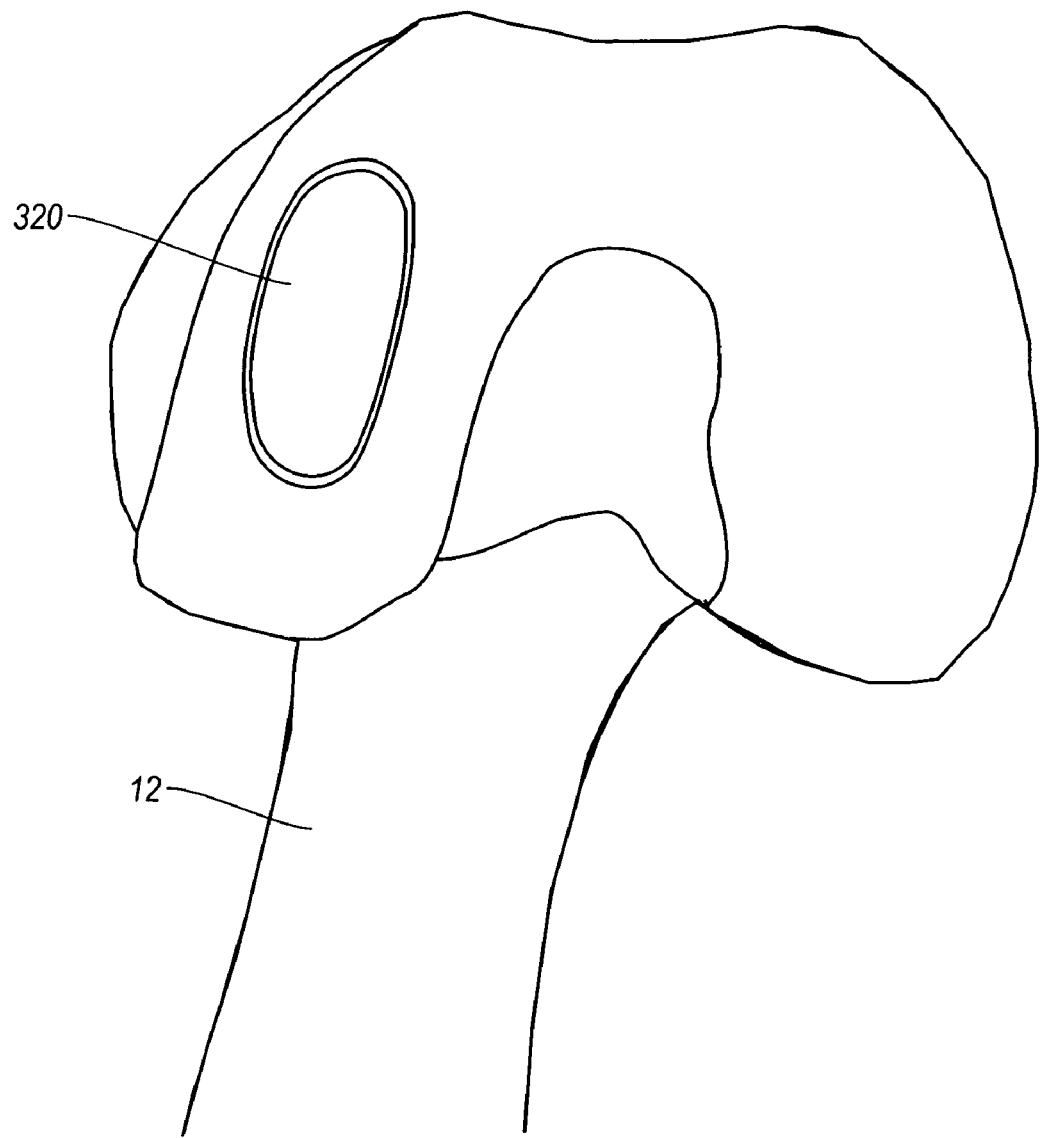
FIG. 16 is a perspective view of the femur shown in FIG. 12 having the implant shown in FIGS. 14 and 15 mounted within the recessed pocket thereof.

Finally, turning to FIG. 16, condylar implant 320 is secured within recessed pocket 310 of femur 12. In the depicted embodiment, this is accomplished by passing line 360 (FIG. 15) within tunnel 300 (FIG. 12) and then using a tensioner and anchor assembly to secure line 360 within tunnel 300. Examples of bone anchors and tensioners that can be used in association with the present invention are disclosed in U.S. patent application Ser. No. 10/901,941. Again, other conventional techniques can be used to secure implant within pocket 310. In such other techniques, line 360 can be eliminated.

Figure 17:
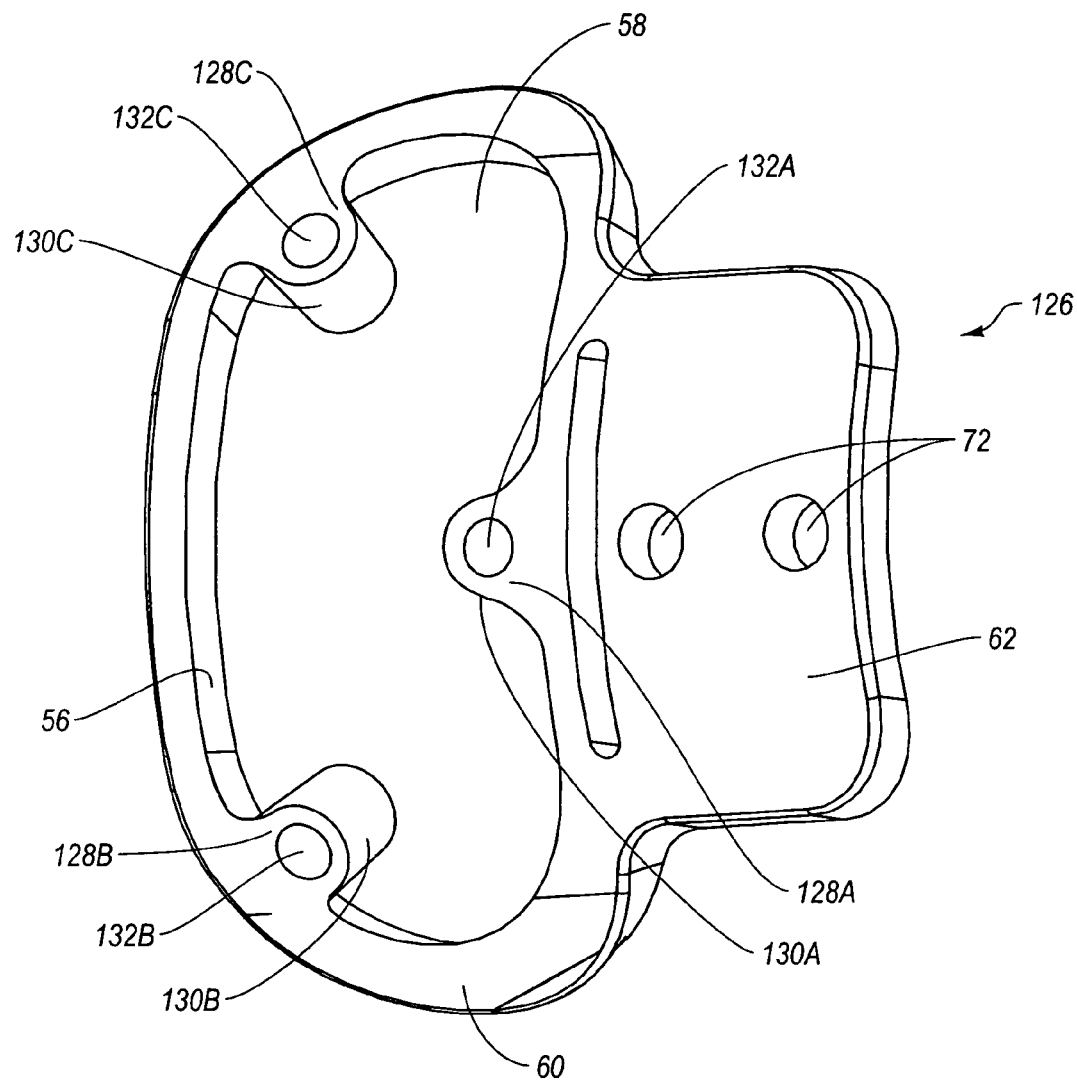
FIG. 17 is a perspective view of an alternative embodiment of the alignment guide shown in FIG. 3.

The above disclosure discusses a number of different guides, mills, templates, and other related instruments, implants and methods. It is appreciated that the individual components and sub-combination of components are novel and can be used independently or mixed and matched with other conventional systems. For example, in one alternative embodiment the function of positioning guide 38 can be integrally incorporated into alignment guide 36. Depicted in FIG. 17 is an alignment guide 126 wherein like elements between alignment guides 36 and 126 are identified by like reference characters.

Alignment guide 126 includes body portion 60 bounding opening 58. Bracket 62 projects from body portion 60 and has coupling holes 72 formed thereon. However, bracket 64 and mounting holes 68A-C have been eliminated. Alignment guide 126 further includes hubs 128A-C projecting from interior surface 56 of body portion 60 into opening 58. Support legs 130A-C downwardly project from hubs 128A-C, respectively, so that support legs 130A-C project below the bottom surface of body portion 60. Extending down through each hub 128A-C and support leg 130A-C is a corresponding mounting hole 132A-C.

During use, alignment guide 126 is positioned on articular cartilage 28 so that support legs 130A-C directly rest against articular cartilage 28 and body portion 60 is suspended above articular cartilage 28. Fasteners, such as screws 93 (FIG. 3), are then passed down through mounting holes 132A-C so as to secure alignment guide 126 to femur 12. Template 150 is then mounted on alignment guide 126 and cutting surface 66 is resected in substantially the same matter as discussed above. After removal of alignment guide 126, the portion of articular cartilage 28 disposed below support legs 130A-C is manually removed, such as with a hand held mill, so as to complete the formation of recessed pocket 310. Because the portion of articular cartilage 28 on which support legs 130A-C rests is ultimately resected, any damage to articular cartilage 28 by support legs 130A-C resting thereagainst or screws penetrating therein, is irrelevant. Further disclosure with regard to this method for mounting a guide is disclosed in U.S. patent application Ser. No. 11/138,016, filed May 26, 2005, entitled Milling System and Method for Resecting a Joint Articulation Surface in the name of Carlyle J. Creger et al., which is incorporated herein by specific reference.

Different features of the present invention provide a number of benefits over conventional systems and methods. For example, in contrast to many conventional processes which require the removal of an entire articulation surface for the mounting of an implant, the present invention enables the resurfacing of an isolated location on the articulation surface. As a result, the procedure is less invasive and recovery time is increased. The milling systems of the present invention enable the formation of the pocket while minimizing retraction of soft tissue, minimizing the amount of bone removal, and minimizing the time required to remove the bone and mount the implant. Using a high speed burr, as opposed to a saw blade or rasp, also has advantages in that the burr requires less effort to cut and can more precisely remove sections of bone. Furthermore, unlike saw blades and rasps which during use often cover a portion of the bone that is desired to be removed, burrs allow for greater visibility of the bone during removal, thereby improving accuracy of bone removal.

The milling system is also unique in that the milling system is either suspended above the articulation surface or is mounted only over the area of the articulation surface that is to be resurfaced. As a result, the potential for unintentional damage to the portion of the surrounding articular surface that is not to be resurfaced is minimized. Another advantage of the present invention is that it provides a system that is easy to mount and use on uneven or irregular surfaces, is easy to operate, and is easy to remove. The present invention also provides other advantages which will be apparent to those skilled in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A milling system for use in resecting at least a portion of a joint articulation surface of a bone, the system having a first configuration and a second configuration, the system comprising:
    an alignment guide comprising a base having a top surface and an opposing bottom surface with an opening extending therebetween;
    a positioning guide removably secured to the alignment guide, the positioning guide having a support portion that terminates at a distal end, the positioning guide being secured to the alignment guide in the first configuration with the distal end being inserted into the opening at the top surface of the alignment guide and passed through the opening of the alignment guide so as to extend below the bottom surface thereof, the distal end of the support portion being freely and openly exposed below the bottom surface of the alignment guide in the first configuration, whereby the distal end can be selectively placed directly on a bone at a predetermined location;
    a connector that removably secures the positioning guide to the alignment guide;
    a template removably secured to the alignment guide, the template having a top surface and an opposing bottom surface with a plurality of guide paths extending therebetween, the template being secured to the alignment guide in the second configuration so that at least a portion of the plurality of guide paths is aligned with the predetermined location of the bone; and
    means for removably mounting the alignment guide to a bone.

2. The milling system as recited in claim 1, wherein the alignment guide further comprises a bracket projecting from the base and having at least one mounting hole extending therethrough.

3. The milling system as recited in claim 1, wherein the base completely encircles the opening of the alignment guide.

4. The milling system as recited in claim 1, wherein the support portion of the positioning guide forms a continuous loop.

5. The milling system as recited in claim 1, wherein the support portion of the positioning guide comprises at least three spaced apart support legs.

6. The milling system as recited in claim 1, wherein the means for removably mounting comprises a plurality of fasteners that pass through mounting holes formed on the alignment guide to engage the bone.

7. The milling system as recited in claim 6, wherein the fasteners comprise screws.

8. The milling system as recited in claim 1, wherein the distance through the opening is less than the distance across the opening.

9. A milling system for use in resecting at least a portion of a joint articulation surface of a bone, the system comprising:
    an alignment guide comprising a base having a top surface and an opposing bottom surface with an opening extending therebetween;
    a positioning guide removably secured to the alignment guide, the positioning guide having a support portion that terminates at a distal end, the distal end being inserted into the opening at the top surface of the alignment guide and passed through the opening of the alignment guide so as to extend below the bottom surface thereof, the distal end of the support portion being freely and openly exposed below the bottom surface of the alignment guide, whereby the distal end can be selectively placed directly on a bone;
    a connector that removably secures the positioning guide to the alignment guide, wherein the connector comprises an elongated handle removably coupling the positioning guide to the alignment guide; and
    means for removably mounting the alignment guide to a bone.

10. The milling system as recited in claim 9, wherein the elongated handle removably couples the positioning guide to the alignment guide using coupling holes formed on the top surface of the alignment guide.

11. A milling system for use in resecting at least a portion of a joint articulation surface of a bone, the system having a first configuration and a second configuration, the system comprising:
    an alignment guide comprising a base having a top surface and an opposing bottom surface with a first opening extending therebetween;
    a positioning guide removably secured to the alignment guide, the positioning guide having a support portion that comprises a continuous loop that bounds a second opening or at least two spaced apart support legs, the positioning guide being secured to the alignment guide in the first configuration with the continuous loop or the at least two spaced apart support legs being inserted into the first opening at the top surface of the alignment guide and passed through the first opening of the alignment guide so as to extend beyond the bottom surface thereof;
    a connector that removably secures the positioning guide to the alignment guide;
    a template removably secured to the alignment guide, the template having a top surface and an opposing bottom surface with a plurality of guide paths extending therebetween, the template being secured to the alignment guide in the second configuration so that the plurality of guide paths are aligned with the first opening of the alignment guide; and a fastener configured to removably mount the alignment guide to a bone.

12. The milling system as recited in claim 11, wherein the continuous loop or the at least two support legs comprises a continuous loop that is at least partially disposed within the first opening.

13. The milling system as recited in claim 11, wherein the continuous loop or the at least two support legs comprises at least two support legs that are at least partially disposed within the first opening.

14. A milling system for use in resecting at least a portion of a joint articulation surface of a bone, the system comprising:
an alignment guide having a top surface and an opposing bottom surface with an opening extending from the top surface to the bottom surface and one or more coupling holes also extending from the top surface to the bottom surface; and
a positioning guide removably disposed on the alignment guide, the positioning guide comprising:
a support portion passing through the opening of the alignment guide and extending below the bottom surface thereof when the positioning guide is disposed on the alignment guide; and
an arm extending from the support portion, the arm being at least partially disposed above the top surface of the alignment guide and containing one or more coupling holes that align with the one or more coupling holes of the alignment guide when the positioning guide is disposed on the alignment guide; and
a template removably disposed on the alignment guide, the template having a top surface and an opposing bottom surface with a plurality of guide paths extending therebetween, the template containing one or more coupling holes that align with the one or more coupling holes of the alignment guide when the template is disposed on the alignment guide.

15. The milling system as recited in claim 14, further comprising a connector that removably secures the positioning guide to the alignment guide via the coupling holes on the positioning guide and the alignment guide.

16. The milling system as recited in claim 14, wherein the support portion of the positioning guide forms a continuous loop.

17. The milling system as recited in claim 14, wherein the support portion of the positioning guide comprises at least three spaced apart support legs.

18. A milling system for use in resecting at least a portion of a joint articulation surface of a bone, the system comprising:
an alignment guide comprising a base having a top surface and an opposing bottom surface with an opening extending therebetween;
a positioning guide removably secured to the alignment guide, the positioning guide having a support portion passing through the opening of the alignment guide such that at least a first portion of the support portion extends above the top surface of the alignment guide and at least a second portion of the support portion extends below the bottom surface of the alignment guide;
a connector that removably secures the positioning guide to the alignment guide;
a template configured for securement to the alignment guide when the positioning guide is removed from the alignment guide, the template having a top surface and an opposing bottom surface with a plurality of guide paths extending therebetween; and
means for removably mounting the alignment guide to a bone.

19. The milling system as recited in claim 18, wherein the support portion of the positioning guide forms a continuous loop.

20. The milling system as recited in claim 18, wherein the support portion of the positioning guide comprises at least three spaced apart support legs.

21. A milling system for use in resecting at least a portion of a joint articulation surface of a bone, the system comprising:
an alignment guide comprising a base having a top surface and an opposing bottom surface with an opening extending therebetween;
a positioning guide removably secured to the alignment guide, the positioning guide having a support portion that terminates at a distal end, the distal end being inserted into the opening at the top surface of the alignment guide and passed through the opening of the alignment guide so as to extend below the bottom surface thereof, the distal end of the support portion being freely and openly exposed below the bottom surface of the alignment guide, whereby the distal end can be selectively placed directly on a bone;
a connector that removably secures the positioning guide to the alignment guide;
means for removably mounting the alignment guide to a bone, wherein the means for removably mounting comprises a plurality of fasteners that pass through mounting holes formed on the alignment guide to engage the bone; and
a plurality of guide sleeves at least partially disposed within the mounting holes to guide the fasteners to the bone.

22. A milling system for use in resecting at least a portion of a joint articulation surface of a bone, the system comprising:
an alignment guide having a top surface and an opposing bottom surface with an opening extending from the top surface to the bottom surface and one or more coupling holes also extending from the top surface to the bottom surface; and
a positioning guide removably disposed on the alignment guide, the positioning guide comprising:
a support portion passing through the opening of the alignment guide and extending below the bottom surface thereof; and
an arm extending from the support portion, the arm being at least partially disposed above the top surface of the alignment guide and containing one or more coupling holes that align with the one or more coupling holes of the alignment guide; and
a connector that removably secures the positioning guide to the alignment guide via the coupling holes on the positioning guide and the alignment guide, wherein the connector removably secures the positioning guide to the alignment guide by threaded connection.

23. A milling system for use in resecting at least a portion of a joint articulation surface of a bone, the system having a first configuration and a second configuration, the system comprising:
an alignment guide having a top surface and an opposing bottom surface;
a positioning guide removably secured to the alignment guide, the positioning guide having a support portion that terminates at a distal end, the positioning guide being secured to the alignment guide in the first configuration with the distal end extending below the bottom surface of the alignment guide to contact the bone, whereby the bottom surface of the alignment guide is suspended above the bone in the first configuration;

a connector that removably secures the positioning guide to the alignment guide;

a template removably secured to the alignment guide, the template having a top surface and an opposing bottom surface with a plurality of guide paths extending therebetween, the template being secured to the alignment guide in the second configuration; and means for removably mounting the alignment guide to the bone such that the alignment guide remains suspended above the bone in the second configuration when the positioning guide is removed.

* * * * *